(12) United States Patent
Hopkins

(10) Patent No.: US 11,180,499 B2
(45) Date of Patent: Nov. 23, 2021

(54) PHOSPHODIESTERASE INHIBITORS

(71) Applicant: BOARD OF REGENTS OF THE UNIVERSITY OF NEBRASKA, Lincoln, NE (US)

(72) Inventor: Corey Hopkins, Omaha, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 0 days.

(21) Appl. No.: 17/227,597

(22) Filed: Apr. 12, 2021

(65) Prior Publication Data

US 2021/0230160 A1 Jul. 29, 2021

Related U.S. Application Data

(63) Continuation of application No. PCT/US2019/055780, filed on Oct. 11, 2019.

(60) Provisional application No. 62/744,857, filed on Oct. 12, 2018.

(51) Int. Cl.
| | |
|---|---|
| *C07D 471/04* | (2006.01) |
| *A61K 31/5377* | (2006.01) |
| *A61K 31/4353* | (2006.01) |
| *C07D 519/00* | (2006.01) |

(52) U.S. Cl.
CPC ......... *C07D 471/04* (2013.01); *C07D 519/00* (2013.01)

(58) Field of Classification Search
CPC .............. C07D 471/04; A61K 31/5377; A61K 31/4353
USPC .................................................. 514/210.16
See application file for complete search history.

(56) References Cited

U.S. PATENT DOCUMENTS

| | | | |
|---|---|---|---|
| 5,466,468 A | 11/1995 | Schneider et al. | |
| 7,622,466 B2 * | 11/2009 | Nettekoven | A61P 25/28 514/234.5 |
| 2009/0005379 A1 | 1/2009 | Nettekoven et al. | |
| 2011/0105464 A1 | 5/2011 | Castanedo et al. | |
| 2011/0183985 A1 | 7/2011 | Li et al. | |
| 2017/0231986 A1 | 8/2017 | Hamdy et al. | |

FOREIGN PATENT DOCUMENTS

WO    WO-2011/163195 A1    12/2011

OTHER PUBLICATIONS

Davis et a., Preparation and characterization of antibodies with specificity for the amino-terminal tetrapeptide sequence of the platelet-derived connective tissue, Biochem. Intl., 10:394-404 (1985).
DeLuca et al., Parenteral Drug-Delivery Systems, pp. 238-250 IN: Banker et al., Pharmaceutics and Pharmacy Practice, Philadelphia, Penn: J.B. Lippincott Company (1982).
Erickson et al., Solid-Phase Peptide Synthesis, pp. 257-527, The Proteins, 3rd Edition, vol. 2 (1976).
Finn et al., The Synthesis of Peptides by Solution Methods with Emphasis on Peptide Hormones, The Proteins, 3rd edition, vol. 2, pp. 106-253 (1976).
International Application No. PCT/US2019/055780, International Search Report and Written Opinion, dated Dec. 6, 2019.
International Application No. PCT/US2019/055780, International Preliminary Report on Patentability, dated Apr. 22, 2021.
Larsen et al., The Merrifield Peptide Synthesis Studied by Near-Infrared Fourier-Transform Raman Spectroscopy, J. Am. Chem. Soc., 115:6247-53 (1993).
Merrifield, "Solid Phase Peptide Synthesis. I. The Synthesis of a Tetrapeptide," J Am Chem Soc 85:2149-2154 (1963).
O'Donnell et al., Solid-Phase unnatural peptide synthesis (UPS), J. Am. Chem. Soc., 118:6070-1 (1996).
Pubchem, CID 123674986, 1-Cyclopentyl-N,N-dimethylpyrrolo[2,3-b]pyridine-2-carboxamide, Jan. 25, 2017.
Smith et al., Solid-phase peptide synthesis and biological activity of bovine thymopoietin II (bTP-II), Int. J. Pept. Protein Res., 44(2):183-91 (1994).
Trissel, ASHP Handbook on Injectable Drugs, pp. 622-630, Fourth Edition, American Society of Hospital Pharmacists (1986).

* cited by examiner

*Primary Examiner* — Niloofar Rahmani
(74) *Attorney, Agent, or Firm* — Marshall, Gerstein & Borun LLP

(57) ABSTRACT

Provided herein are compounds and methods for modulating the phosphodiesterase PDE4. More particularly, provided are selective inhibitors PDE4 and the uses of such inhibitors in regulating diseases and disorders, e.g., to treat cancer, inflammatory diseases, neurological diseases, neurodegenerative diseases, and addiction.

19 Claims, 3 Drawing Sheets

PHOSPHODIESTERASE INHIBITORS

BACKGROUND

Phosphodiesterase 4 (PDE4) are a class of intracellular enzymes that form a critical component of signaling pathways involving multiple physiological and pathophysiological conditions. PDE4s are hydrolytic enzymes responsible for the degradation of second messenger cyclic AMP (cAMP) in many cell types. The PDE4 enzyme family consists of four subtypes (PDE4A-D) coded independently by different genes. PDE4A, PDE4B, and PDE4D are present in the brain. PDE4B plays a critical role in the etiology of disorders like depression and inflammation. The development of novel 1H-pyrrolo[2,3-b] pyridine-2-carboxamide derivatives as selective and potent PDE4 inhibitors is a promising strategy in addressing the need for therapies for various diseases and disorders.

SUMMARY

The disclosure provides compounds of Formula I:

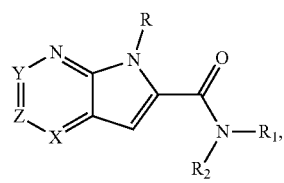

(I)

wherein

X, Y, and Z are each independently N or $CR^3$;

R is $C_{0-6}$alkylene-$C_{6-10}$aryl, $C_{0-6}$alkylene-5-7 membered heteroaryl, $C_{0-6}$alkylene-$C_{3-10}$cycloalkyl, or $C_{0-6}$alkylene-3-10 membered heterocycloalkyl, each optionally substituted by 1-3 $R_4$, wherein the heteroaryl and heterocycloalkyl comprise 1-4 ring heteroatoms independently selected from N, O, and S;

$R_1$ is H, $C_{1-6}$alkyl, or 3-10 membered heterocycloalkyl comprising 1-4 ring heteroatoms independently selected from N, O, and S, and the heterocycloalkyl is optionally substituted by 1-3 $R_5$;

$R_2$ is $C_{1-6}$alkyl, $C_{0-6}$alkylene-$C_{3-10}$cycloalkyl, or $C_{0-6}$alkylene-3-10 membered heterocycloalkyl comprising 1-4 ring heteroatoms independently selected from N, O, and S, wherein the alkyl, cycloalkyl, and heterocycloalkyl are optionally substituted by 1-3 $R_5$; or $R_1$ and $R_2$ together with the nitrogen atom to which they are attached form a 3-10 membered heterocycloalkyl ring comprising 0-2 additional ring heteroatoms independently selected from N, O, and S, wherein the heterocycloalkyl is optionally substituted by 1-3 $R_6$;

each $R_3$ is independently H, $C_{1-6}$alkyl, halogen, $CF_3$, OH, CN, $CONR_7(R_7)$, $SO_2NR_7R_7$, O—$C_{1-6}$alkyl, or O—$C_{6-10}$aryl, and the aryl is optionally substituted with 1-3 $R_5$;

each $R_4$ is independently $C_{1-6}$alkyl, halogen, $CF_3$, CN, $CONHR_7$, $SO_2NR_7R_7$, O—$C_{1-6}$alkyl, or O—$C_{6-10}$aryl;

each of $R_5$ and $R_6$ is independently $C_{1-6}$alkyl, halogen, $CF_3$, CN, OH, or O—$C_{1-6}$alkyl; and each $R_7$ is independently H, $C_{1-6}$alkyl, $C_{0-6}$alkylene-$C_{6-10}$aryl, $C_{0-6}$alkylene-5-7 membered heteroaryl, $C_{0-6}$alkylene-$C_{3-10}$cycloalkyl, or $C_{0-6}$alkylene-3-10 membered heterocycloalkyl, each aryl, heteroaryl, cycloalkyl, and heterocycloalkyl is optionally substituted by 1-3 $R_5$, and the heteroaryl and heterocycloalkyl comprise 1-4 ring heteroatoms independently selected from N, O, and S.

In some embodiments, R is $C_{0-6}$alkylene-$C_{6-10}$aryl or $C_{0-6}$alkylene-5-10 membered heteroaryl. In some embodiments, R is $C_{6-10}$aryl or 5-7 membered heteroaryl. In some embodiments, R is phenyl. In some embodiments, R is dichlorophenyl. In some embodiments, R is

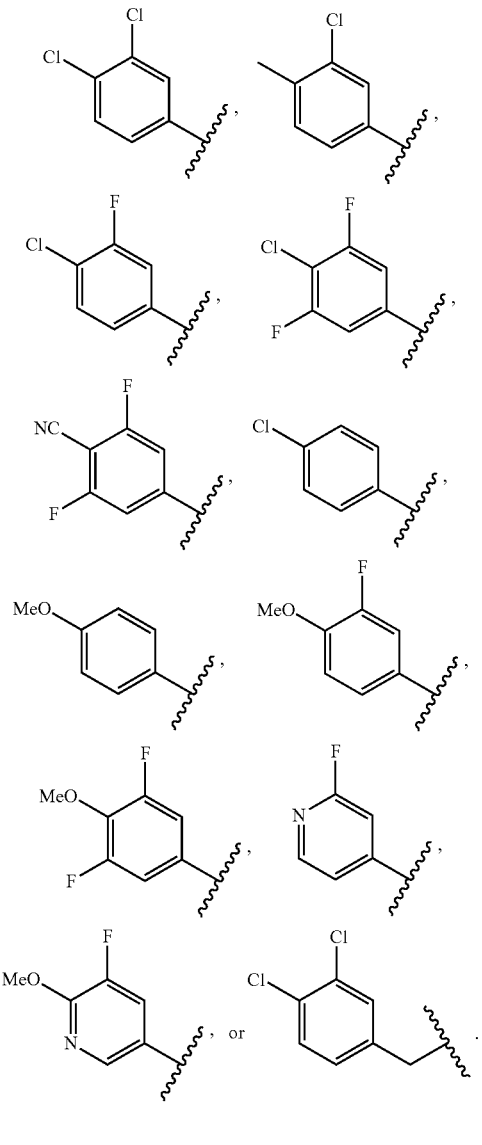

In some embodiments, R is

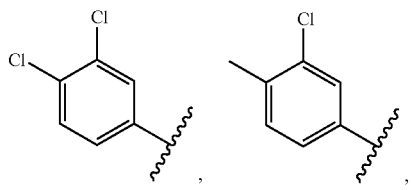

-continued

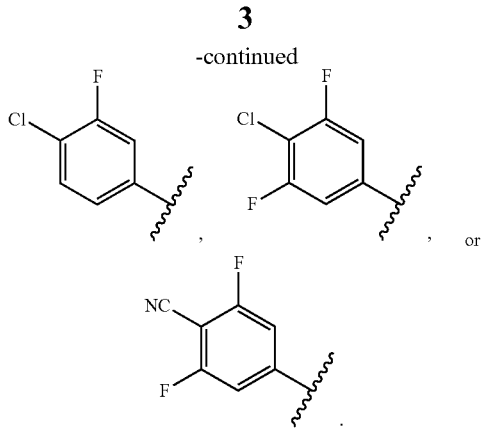

In some embodiments, R is

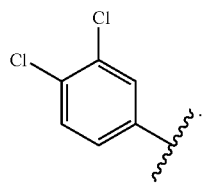 [SMILES: *c1ccc(Cl)c(Cl)c1]

Further provided herein are methods of using the compounds to inhibit PDE4. In one embodiment the compounds of the present disclosure inhibit one or more specific subtype of PDE4 including PDE4A, PDE4B, PDE4C, and PDE4D. In some embodiments, the compounds of the present disclosure inhibit PDE4B and/or PDE4D.

Other aspects of the disclosure include a compound as disclosed herein for use in the preparation of a medicament for treating or preventing a disease or disorder capable of being modulated by PDE4 inhibition in a subject, and the use of a compound as disclosed herein in a method of treating or preventing a disease or disorder capable of being modulated by PDE4 inhibition in a subject.

DETAILED DESCRIPTION

Figure 1:
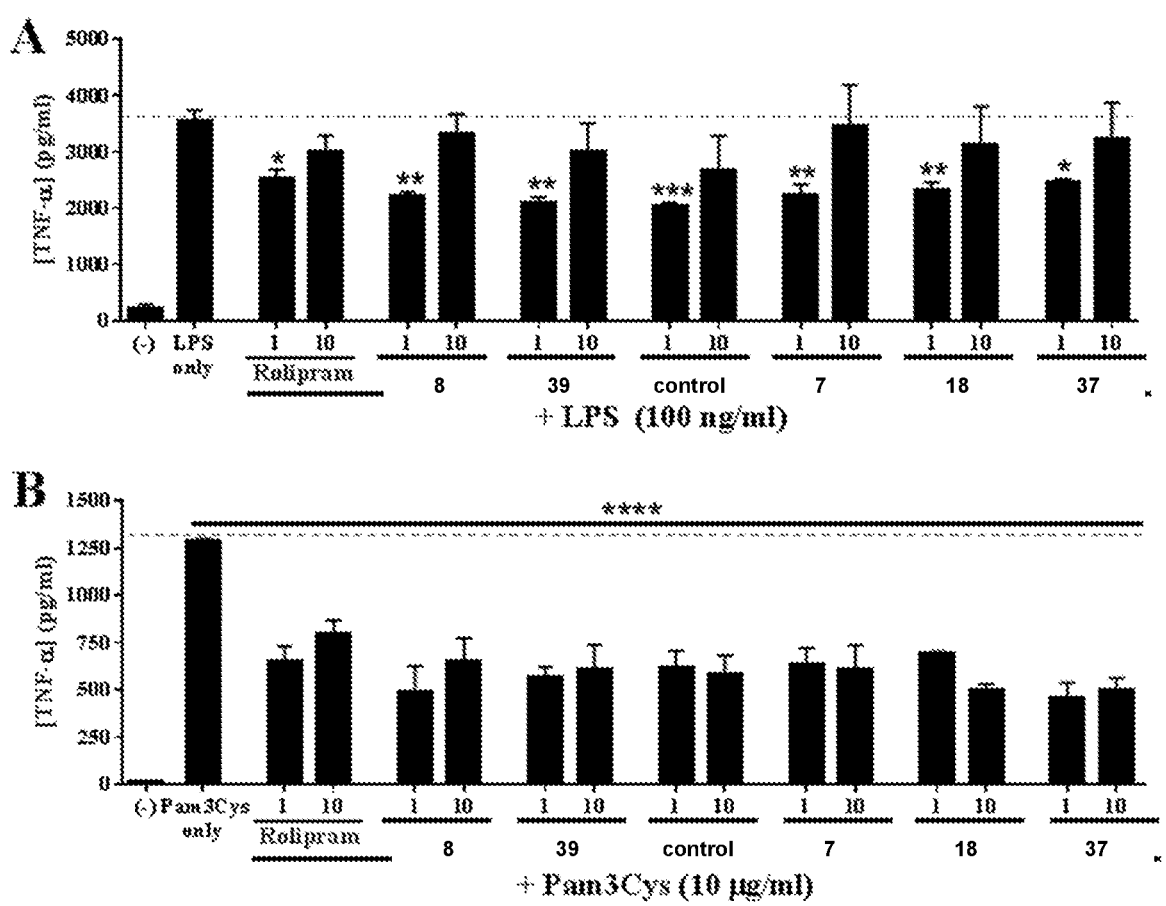
FIG. 1 shows the effect of (from left to right) compounds 8 and 39, a control (3-(3-chloro-4-methylphenyl)-N-cyclopropyl-3H-imidazo[4,5-b]pyridine-2-carboxamide), and compounds 7, 18, and 37 on inhibition of macrophage pro-inflammatory activity. Bone marrow-derived macrophages were unstimulated (-) or pre-treated with the indicated concentrations of the well-characterized PDE4 inhibitor rolipram or target compounds (1 or 10 μM) for 30 min prior to stimulation with (A) lipopolysaccharide (LPS) (100 ng/ml) or (B) synthetic lipopeptide (Pam3Cys) (10 μg/ml).

Provided herein are small molecule inhibitors of PDE4 and methods of use thereof. In one embodiment the compounds of the present disclosure inhibit one or more specific subtype of PDE4 including PDE4A, PDE4B, PDE4C, and PDE4D. In some embodiments, the compounds of the present disclosure inhibit PDE4B and/or PDE4D. These compounds are useful in the treatment of a variety of diseases and disorders, including but not limited to cancer, neurodegenerative diseases, addiction, autoimmune disorders, inflammatory disorders, depression and depressive disorders, and anxiety disorders.

Compounds of the Disclosure

The disclosure provides compounds of Formula I:

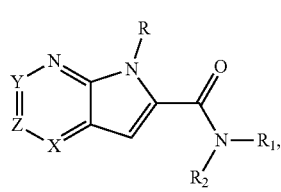

wherein
X, Y, and Z are each independently N or $CR^3$;
R is $C_{0-6}$alkylene-$C_{6-10}$aryl, $C_{0-6}$alkylene-5-7 membered heteroaryl, $C_{0-6}$alkylene-$C_{3-10}$cycloalkyl, or $C_{0-6}$alkylene-3-10 membered heterocycloalkyl, each optionally substituted by 1-3 $R_4$, wherein the heteroaryl and heterocycloalkyl comprise 1-4 ring heteroatoms independently selected from N, O, and S;
$R_1$ is H, $C_{1-6}$alkyl, or 3-10 membered heterocycloalkyl comprising 1-4 ring heteroatoms independently selected from N, O, and S, and the heterocycloalkyl is optionally substituted by 1-3 $R_5$;
$R_2$ is $C_{1-6}$alkyl, $C_{0-6}$alkylene-$C_{3-10}$cycloalkyl, or $C_{0-6}$alkylene-3-10 membered heterocycloalkyl comprising 1-4 ring heteroatoms independently selected from N, O, and S, wherein the alkyl, cycloalkyl, and heterocycloalkyl are optionally substituted by 1-3 $R_5$; or
$R_1$ and $R_2$ together with the nitrogen atom to which they are attached form a 3-10 membered heterocycloalkyl ring comprising 0-2 additional ring heteroatoms independently selected from N, O, and S, wherein the heterocycloalkyl is optionally substituted by 1-3 $R_6$;
each $R_3$ is independently H, $C_{1-6}$alkyl, halogen, $CF_3$, OH, CN, $CONR_7(R_7)$, $SO_2NR_7R_7$, O—$C_{1-6}$alkyl, or O—$C_{6-10}$aryl, and the aryl is optionally substituted with 1-3 $R_5$;
each $R_4$ is independently $C_{1-6}$alkyl, halogen, $CF_3$, CN, $CONHR_7$, $SO_2NR_7R_7$, O—$C_{1-6}$alkyl, or O—$C_{6-10}$aryl;
each of $R_5$ and $R_6$ is independently $C_{1-6}$alkyl, halogen, $CF_3$, CN, OH, or O—$C_{1-6}$alkyl; and
each $R_7$ is independently H, $C_{1-6}$alkyl, $C_{0-6}$alkylene-$C_{6-10}$aryl, $C_{0-6}$alkylene-5-7 membered heteroaryl, $C_{0-6}$alkylene-$C_{3-10}$cycloalkyl, or $C_{0-6}$alkylene-3-10 membered heterocycloalkyl, each aryl, heteroaryl, cycloalkyl, and heterocycloalkyl is optionally substituted by 1-3 $R_5$, and the heteroaryl and heterocycloalkyl comprise 1-4 ring heteroatoms independently selected from N, O, and S.

As used herein, the term "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_{1-6}$ alkyl refers to an alkyl group having a number of carbon atoms encompassing the entire range (e.g., 1 to 6 carbon atoms), as well as all subgroups (e.g., 1-6, 2-5, 1-4, 3-6, 1, 2, 3, 4, 5, and 6 carbon atoms). Nonlimiting examples of alkyl groups include, methyl, ethyl, n-propyl, isopropyl, n-butyl, sec-butyl (2-methylpropyl), and t-butyl (1,1-dimethylethyl).

Unless otherwise indicated, an alkyl group can be an unsubstituted alkyl group or a substituted alkyl group.

The term "alkylene" used herein refers to an alkyl group having a substituent. For example, an alkylene group can be —CH$_2$CH$_2$— or —CH$_2$—. The term O$_n$ means the alkylene group has "n" carbon atoms. For example, 01-6 alkylene refers to an alkylene group having a number of carbon atoms encompassing the entire range, as well as all subgroups, as previously described for "alkyl" groups. Unless otherwise indicated, an alkylene group can be an unsubstituted alkylene group or a substituted alkylene group.

As used herein, the term "cycloalkyl" refers to an aliphatic cyclic hydrocarbon group containing three to ten carbon atoms (e.g., 3, 4, 5, 6, 7, 8, 9, or 10 carbon atoms). The term O$_n$ means the cycloalkyl group has "n" carbon atoms. For example, C$_5$ cycloalkyl refers to a cycloalkyl group that has 5 carbon atoms in the ring. C$_{3-10}$ cycloalkyl refers to cycloalkyl groups having a number of carbon atoms encompassing the entire range (e.g., 3 to 10 carbon atoms), as well as all subgroups (e.g., 3-9, 3-8, 3-7, 3-6, 3-5, 3-4, 4-9, 4-8, 4-7, 4-6, 4-5, 5-9, 5-8, 5-7, 5-6, 6-9, 6-8, 6-7, 7-9, 7-8, 8-9, 3, 4, 5, 6, 7, 8, 9, and 10 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group. For example, a cycloalkyl group can be a cyclobutyl ring substituted with one or two fluoro groups. The cycloalkyl groups described herein can be isolated or fused to another cycloalkyl group, a heterocycloalkyl group, an aryl group and/or a heteroaryl group. The fusion can be e.g., a spiro fusion. When a cycloalkyl group is fused to another cycloalkyl group, then each of the cycloalkyl groups can contain three to ten carbon atoms unless specified otherwise.

As used herein, the term "heterocycloalkyl" is defined similarly as cycloalkyl, except the ring contains one to four heteroatoms independently selected from oxygen, nitrogen, and sulfur. In particular, the term "heterocycloalkyl" refers to a ring containing a total of three to ten atoms (e.g., three to seven, or five to ten), of which 1, 2, 3 or 4 of those atoms are heteroatoms independently selected from the group consisting of oxygen, nitrogen, and sulfur, and the remaining atoms in the ring are carbon atoms. Nonlimiting examples of heterocycloalkyl groups include azetidine, piperdine, pyrazolidine, tetrahydrofuran, tetrahydropyran, dihydrofuran, morpholine, and the like. Unless otherwise indicated, a heterocycloalkyl group can be an unsubstituted heterocycloalkyl group or a substituted heterocycloalkyl group. For example, a heterocycloalkyl group can be an azetidine ring substituted with one or two fluoro groups.

As used herein, the term "aryl" refers to a monocyclic aromatic group, such as phenyl. Unless otherwise indicated, an aryl group can be unsubstituted or substituted with one or more, and in particular one to four groups independently selected from, for example, alkyl, halogen, CF$_3$, CN, OH, amide, sulfonamide, O-alkyl, or O-aryl. Aryl groups can be isolated (e.g., phenyl) or fused to another aryl group (e.g., naphthyl, anthracenyl), a cycloalkyl group (e.g. tetraydronaphthyl), a heterocycloalkyl group, and/or a heteroaryl group. Exemplary aryl groups include, but are not limited to, phenyl, chlorophenyl, dichlorophenyl, methylphenyl, methoxyphenyl, trifluoromethylphenyl, 2,4-methoxychlorophenyl, and the like.

As used herein, the term "heteroaryl" refers to a monocyclic aromatic ring having 5 to 7 total ring atoms, and containing one to four heteroatoms selected from nitrogen, oxygen, and sulfur atom in the aromatic ring. Unless otherwise indicated, a heteroaryl group can be unsubstituted or substituted with one or more, and in particular one to four groups independently selected from, for example, alkyl, halogen, CF$_3$, CN, OH, amide, sulfonamide, O-alkyl, or O-aryl. Examples of heteroaryl groups include, but are not limited to, thienyl, furyl, pyridyl, pyrrolyl, oxazolyl, triazinyl, triazolyl, isothiazolyl, isoxazolyl, imidazolyl, pyrazinyl, pyrimidinyl, thiazolyl, and thiadiazolyl.

In some cases, at least one of X, Y, and Z is CR$^3$. In some cases, at least one of X, Y, and Z is N. In some cases, X, Y, and Z are each CR$^3$. In some cases, each R$_3$ is independently H, C$_{1-6}$alkyl, halogen, CF$_3$, OH, CN, or O—C$_{1-6}$alkyl. In some cases, at least one R$_3$ is H. In some cases, at least one R$_3$ is C$_{1-6}$alkyl. In some cases, at least one R$_3$ is halogen. In some cases, at least one R$_3$ is CF$_3$. In some cases, at least one R$_3$ is OH. In some cases, at least one R$_3$ is CN. In some cases, at least one R$_3$ is —O—C$_{1-6}$alkyl. In some cases, X, Y, and Z are each CH.

In some cases, R is C$_{0-6}$alkylene-C$_{6-10}$aryl or C$_{0-6}$alkylene-5-10 membered heteroaryl. In some cases, R is C$_{1-6}$alkylene-C$_{6-10}$aryl or C$_{1-6}$alkylene-5-10 membered heteroaryl. In some cases, R is C$_1$alkylene-C$_{6-10}$aryl or C$_1$alkylene-5-10 membered heteroaryl. In some cases, R is C$_{6-10}$aryl or 5-7 membered heteroaryl. In some cases, R is C$_{6-10}$aryl or 5-7 membered heteroaryl. In some cases, R is phenyl. In some cases, R is dichlorophenyl. In some cases, R is

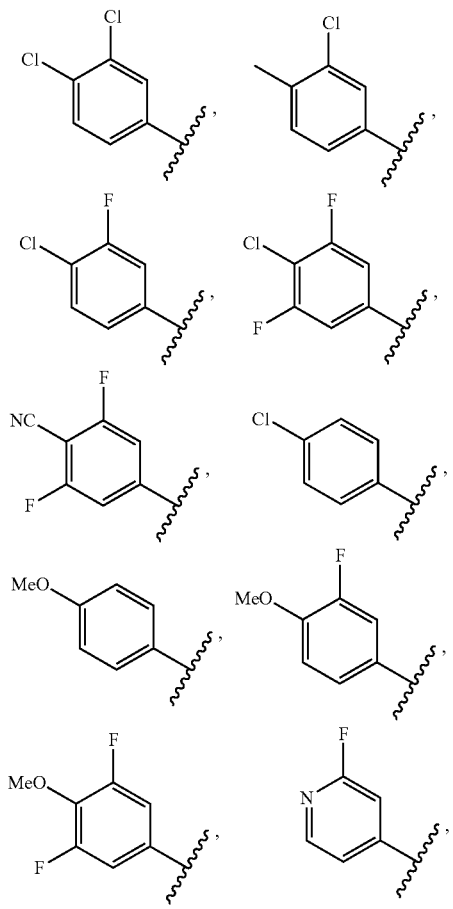

-continued

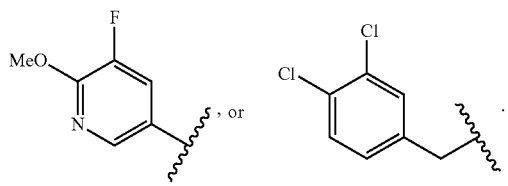

In some cases, R is

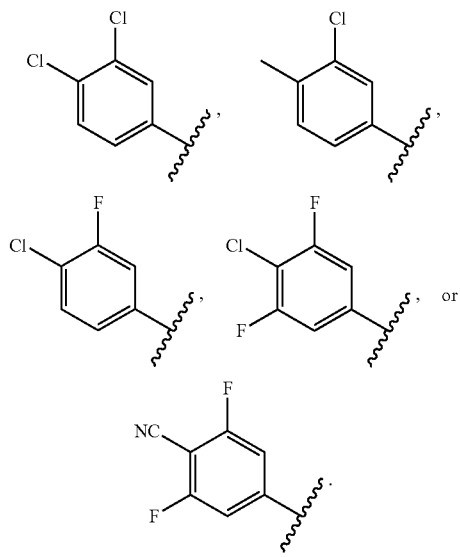

In some case, R is

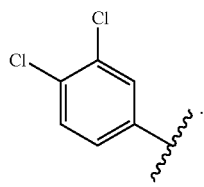

In some cases, R is substituted by 1 to 3 $R_4$. In some cases, R is substituted by 1 $R_4$. In some cases, R is substituted by 2 $R_4$. In some cases, R is substituted by 3 $R_4$.

In some cases, each $R_4$ is independently $C_{1-6}$alkyl, O—$C_{1-6}$alkyl, halogen, or CN. In some cases, at least one $R_4$ is halogen. In some cases, each $R_4$ is halogen. In some cases, at least one $R_4$ is fluoro. In some cases, at least one $R_4$ is chloro. In some cases, at least one $R_4$ is $C_{1-6}$alkyl. In some cases, at least one $R_4$ is methyl. In some cases, at least one $R_4$ is, O—$C_{1-6}$alkyl. In some cases, at least one $R_4$ is CN or OMe. In some cases, at least one $R_4$ is CN. In some cases, at least one $R_4$ is OMe.

In some cases, $R_1$ is H. In some cases, $R_1$ is $C_{1-6}$alkyl.

In some cases, $R_2$ is $C_{0-6}$alkylene-$C_{3-10}$cycloalkyl or $C_{0-6}$alkylene-3-10 membered heterocycloalkyl. In some cases, $R_2$ is $C_{3-10}$cycloalkyl. In some cases, $R_2$ is $C_{3-6}$cycloalkyl. In some cases, $R_2$ is cyclopropyl. In some cases, $R_2$ is cyclobutyl. In some cases, $R_2$ is

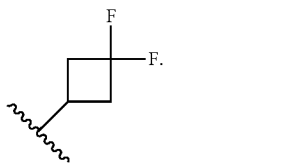

In some cases, $R_2$ is substituted by 1-3 $R_5$. In some cases, $R_2$ is substituted by 1 $R_5$. In some cases, $R_2$ is substituted by 2 $R_5$. In some cases, $R_2$ is substituted by 3 $R_5$. In some cases, at least one $R_5$ is halogen. In some cases, each $R_5$ is halogen. In some cases, at least one $R_5$ is fluoro. In some cases, each $R_5$ is fluoro.

In some cases, $R_1$ and $R_2$ together with the nitrogen atom to which they are attached form a 3-10 membered heterocycloalkyl ring. In some cases, $R_1$ and $R_2$ together with the atom to which they are attached form a 3 membered heterocycloalkyl ring. In some cases, $R_1$ and $R_2$ together with the atom to which they are attached form a 4 membered heterocycloalkyl ring. In some cases, $R_1$ and $R_2$ together with the atom to which they are attached form a 5 membered heterocycloalkyl ring. In some cases, $R_1$ and $R_2$ together with the atom to which they are attached form a 6 membered heterocycloalkyl ring. In some cases, $R_1$ and $R_2$ together with the atom to which they are attached form a 7 membered heterocycloalkyl ring. In some cases, $R_1$ and $R_2$ together with the atom to which they are attached form an 8 membered heterocycloalkyl ring. In some cases, $R_1$ and $R_2$ together with the atom to which they are attached form a 9 membered heterocycloalkyl ring. In some cases, $R_1$ and $R_2$ together with the atom to which they are attached form a 10 membered heterocycloalkyl ring. In some cases, the heterocycloalkyl ring is unsubstituted. In some cases, the heterocycloalkyl ring is substituted by 1-3 $R_6$. In some cases, the heterocycloalkyl ring is substituted by 1 $R_6$. In some cases, the heterocycloalkyl ring is substituted by 2 $R_6$. In some cases, the heterocycloalkyl ring is substituted by 3 $R_6$.

In some cases, $R_6$ is halogen or $CF_3$. In some cases, at least one $R_6$ is halogen. In some cases, each $R_6$ is halogen. In some cases, $R_6$ is fluoro. In some cases, at least one $R_6$ is $CF_3$.

In some cases, $N(R_1)(R_2)$ is

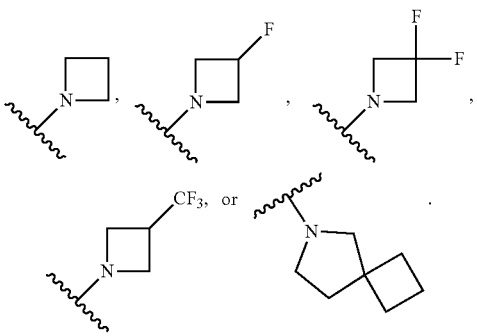

Further provided are compounds as recited in Table A, or a pharmaceutically acceptable salt thereof. Also provided are use of compounds recited in Table A, or a pharmaceutically acceptable salt thereof.

TABLE A

| Compound # | Structure |
| --- | --- |
| 1 | *N-cyclopropyl-1-(3,4-dichlorophenyl)-1H-pyrrolo[2,3-b]pyridine-2-carboxamide* |
| 2 | *N-cyclobutyl-1-(3,4-dichlorophenyl)-1H-pyrrolo[2,3-b]pyridine-2-carboxamide* |
| 3 | *1-(3,4-dichlorophenyl)-N-(3-fluorocyclobutyl)-1H-pyrrolo[2,3-b]pyridine-2-carboxamide* |
| 4 | *1-(3,4-dichlorophenyl)-N-(3,3-difluorocyclobutyl)-1H-pyrrolo[2,3-b]pyridine-2-carboxamide* |

TABLE A-continued

| Compound # | Structure |
| --- | --- |
| 5 | *1-(3,4-dichlorophenyl)-N-(furan-2-ylmethyl)-1H-pyrrolo[2,3-b]pyridine-2-carboxamide* |
| 6 | *(azetidin-1-yl)(1-(3,4-dichlorophenyl)-1H-pyrrolo[2,3-b]pyridin-2-yl)methanone* |
| 7 | *(1-(3,4-dichlorophenyl)-1H-pyrrolo[2,3-b]pyridin-2-yl)(3-fluoroazetidin-1-yl)methanone* |
| 8 | *(1-(3,4-dichlorophenyl)-1H-pyrrolo[2,3-b]pyridin-2-yl)(3,3-difluoroazetidin-1-yl)methanone* |

TABLE A-continued
| Compound # | Structure |
|---|---|
| 9 | 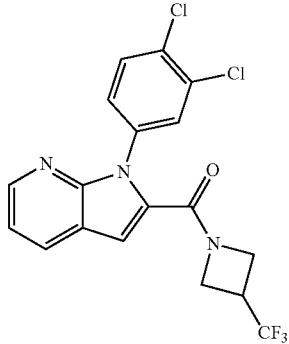 [SMILES: O=C(c1cc2cccnc2n1-c1ccc(Cl)c(Cl)c1)N1CC(C(F)(F)F)C1] |
| 10 | 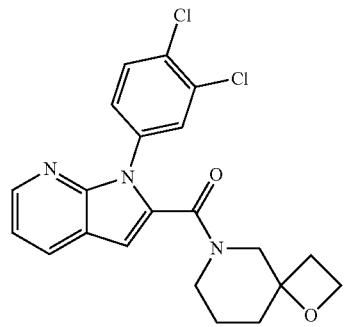 |
| 11 | 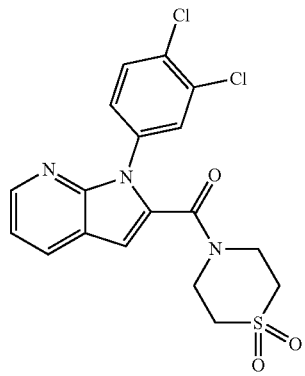 |
| 12 | 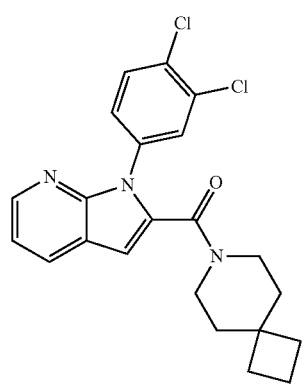 [SMILES: O=C(c1cc2cccnc2n1-c1ccc(Cl)c(Cl)c1)N1CCC2(CCC2)CC1] |
| 13 | 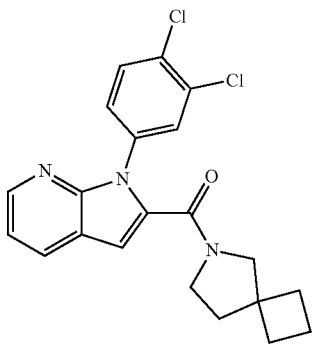 [SMILES: O=C(c1cc2cccnc2n1-c1ccc(Cl)c(Cl)c1)N1CCC2(CCC2)C1] |
| 14 | 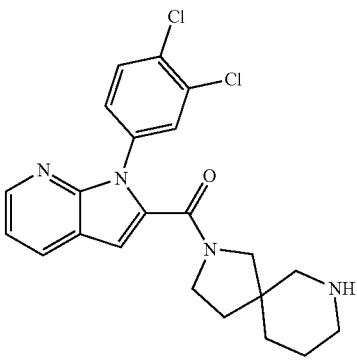 [SMILES: O=C(c1cc2cccnc2n1-c1ccc(Cl)c(Cl)c1)N1CCC2(CCCNC2)C1] |
| 15 | 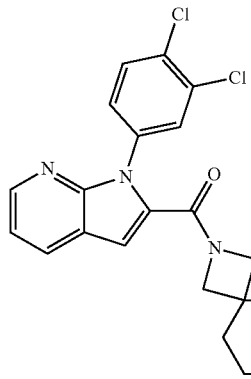 |
| 16 | 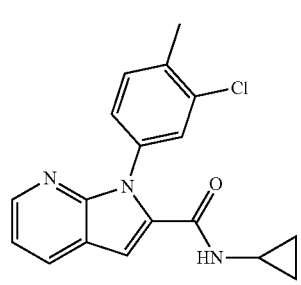 [SMILES: Cc1ccc(-n2c(C(=O)NC3CC3)cc3cccnc32)cc1Cl] |

TABLE A-continued

| Compound # | Structure |
|---|---|
| 17 | 1-(3-chloro-4-methylphenyl)-N-cyclobutyl-1H-pyrrolo[2,3-b]pyridine-2-carboxamide |
| 18 | 1-(3-chloro-4-methylphenyl)-N-(3-fluorocyclobutyl)-1H-pyrrolo[2,3-b]pyridine-2-carboxamide |
| 19 | 1-(3-chloro-4-methylphenyl)-N-(3,3-difluorocyclobutyl)-1H-pyrrolo[2,3-b]pyridine-2-carboxamide |
| 20 | 1-(3-chloro-4-methylphenyl)-2-(3-fluoroazetidine-1-carbonyl)-1H-pyrrolo[2,3-b]pyridine |
| 21 | 1-(4-chloro-3,5-difluorophenyl)-N-cyclopropyl-1H-pyrrolo[2,3-b]pyridine-2-carboxamide |

TABLE A-continued

| Compound # | Structure |
|---|---|
| 22 | 1-(4-chloro-3,5-difluorophenyl)-N-cyclobutyl-1H-pyrrolo[2,3-b]pyridine-2-carboxamide |
| 23 | 1-(4-chloro-3,5-difluorophenyl)-N-(3-fluorocyclobutyl)-1H-pyrrolo[2,3-b]pyridine-2-carboxamide |
| 24 | 1-(4-chloro-3,5-difluorophenyl)-N-(3,3-difluorocyclobutyl)-1H-pyrrolo[2,3-b]pyridine-2-carboxamide |
| 25 | 1-(4-chloro-3,5-difluorophenyl)-2-(3-fluoroazetidine-1-carbonyl)-1H-pyrrolo[2,3-b]pyridine |
| 26 | 1-(4-cyano-3,5-difluorophenyl)-N-cyclopropyl-1H-pyrrolo[2,3-b]pyridine-2-carboxamide |

TABLE A-continued
| Compound # | Structure |
|---|---|
| 27 | 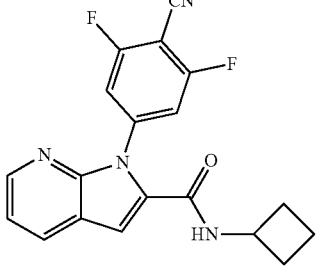 [SMILES: Cc1ccc(-n2c(C(=O)NC3CCC3)cc3cccnc32)cc1Cl] |
| 28 | 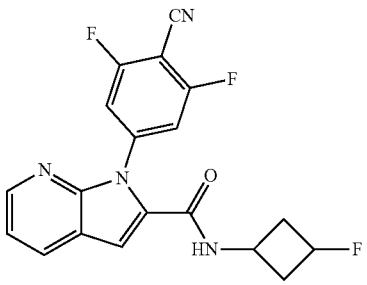 [SMILES: N#Cc1c(F)cc(-n2c(C(=O)NC3CC(F)C3)cc3cccnc32)cc1F] |
| 29 | 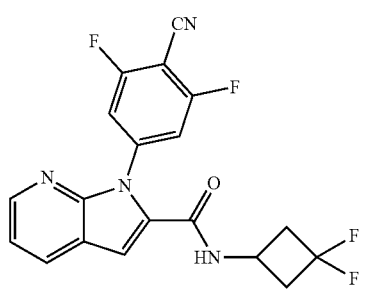 [SMILES: N#Cc1c(F)cc(-n2c(C(=O)NC3CC(F)(F)C3)cc3cccnc32)cc1F] |
| 30 | 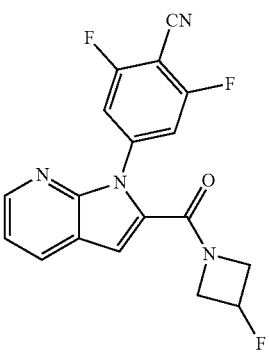 [SMILES: N#Cc1c(F)cc(-n2c(C(=O)N3CC(F)C3)cc3cccnc32)cc1F] |
| 31 | 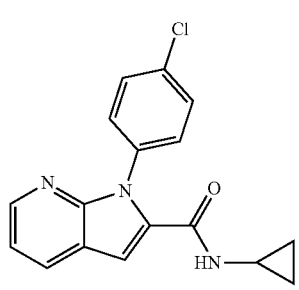 [SMILES: O=C(NC1CC1)c1cc2cccnc2n1-c1ccc(Cl)cc1] |
| 32 | 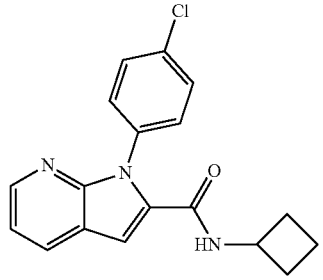 [SMILES: O=C(NC1CCC1)c1cc2cccnc2n1-c1ccc(Cl)cc1] |
| 33 | 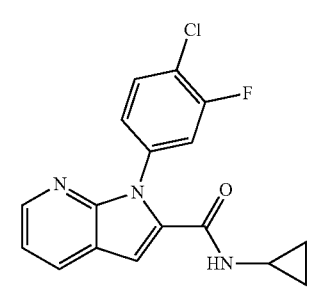 [SMILES: O=C(NC1CC1)c1cc2cccnc2n1-c1ccc(Cl)c(F)c1] |
| 34 | 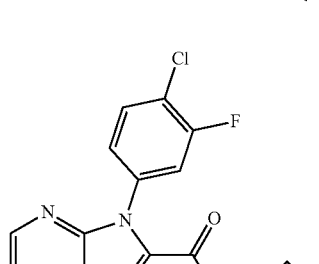 |
| 35 | 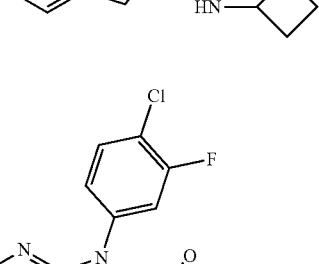 |
| 36 | 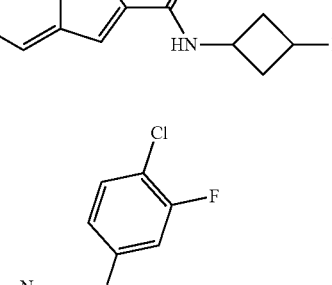 |

TABLE A-continued

| Compound # | Structure |
|---|---|
| 37 | 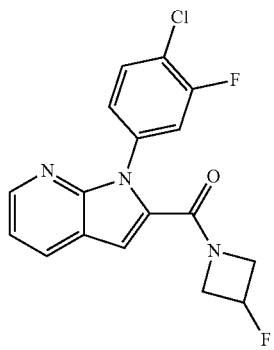 [SMILES: O=C(c1cc2cccnc2n1-c1ccc(Cl)c(F)c1)N1CC(F)C1] |
| 38 | 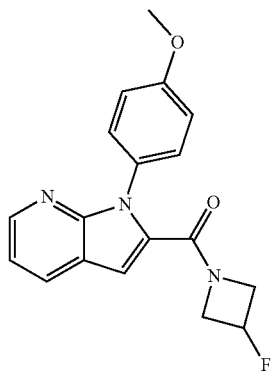 [SMILES: COc1ccc(-n2c(C(=O)N3CC(F)C3)cc3cccnc32)cc1] |
| 39 | 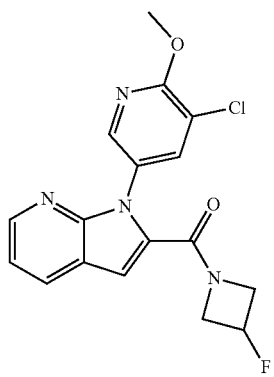 [SMILES: COc1ncc(-n2c(C(=O)N3CC(F)C3)cc3cccnc32)cc1Cl] |
| 40 | 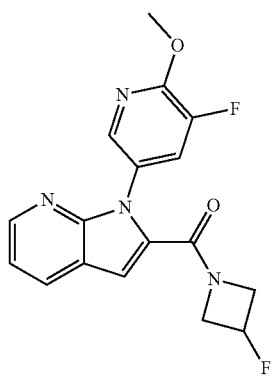 [SMILES: COc1ncc(-n2c(C(=O)N3CC(F)C3)cc3cccnc32)cc1F] |
| 41 | 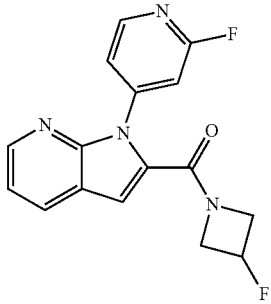 [SMILES: O=C(c1cc2cccnc2n1-c1ccnc(F)c1)N1CC(F)C1] |
| 42 | 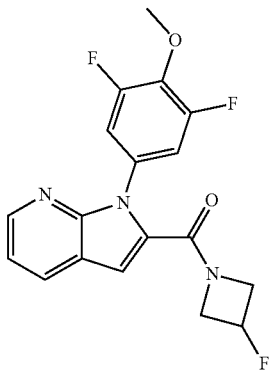 [SMILES: COc1c(F)cc(-n2c(C(=O)N3CC(F)C3)cc3cccnc32)cc1F] |
| 43 | 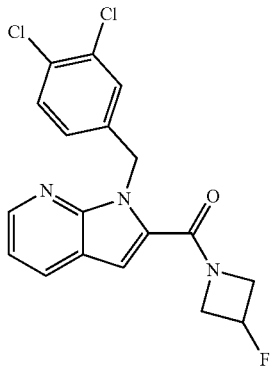 [SMILES: O=C(c1cc2cccnc2n1Cc1ccc(Cl)c(Cl)c1)N1CC(F)C1] |

The compounds disclosed herein can be in the form of a pharmaceutically acceptable salt. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al. describe pharmaceutically acceptable salts in detail in *J. Pharmaceutical Sciences*, 1977, 66, 1-19, which is incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, glutamate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts of compounds containing a carboxylic acid or other acidic functional group can be prepared by reacting with a suitable base. Such salts include, but are not limited to, alkali metal, alkaline earth metal, aluminum salts, ammonium, $N^+(C_{1-4}alkyl)_4$ salts, and salts of organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bis-dehydroabietylamine, glucamine, N-methylglucamine, collidine, quinine, quinoline, and basic amino acids such as lysine and arginine. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Synthesis of Compounds of the Disclosure

The compounds disclosed herein can be prepared in a variety of ways using commercially available starting materials, compounds known in the literature, or from readily prepared intermediates, by employing standard synthetic methods and procedures either known to those skilled in the art, or in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., March's Advanced Organic Chemistry: Reactions, Mechanisms, and Structure, 5$^{th}$ edition, John Wiley & Sons: New York, 2001; and Greene, T. W., Wuts, P. G. M., Protective Groups in Organic Synthesis, 3$^{rd}$ edition, John Wiley & Sons: New York, 1999, are useful and recognized reference textbooks of organic synthesis known to those in the art. For example, the compounds disclosed herein can be synthesized by solid phase synthesis techniques including those described in Merrifield, J. Am. Chem. Soc. 1963; 85:2149; Davis et al., Biochem. Intl. 1985; 10:394-414; Larsen et al., J. Am. Chem. Soc. 1993; 115:6247; Smith et al., J. Peptide Protein Res. 1994; 44: 183; O'Donnell et al., J. Am. Chem. Soc. 1996; 118:6070; Stewart and Young, Solid Phase Peptide Synthesis, Freeman (1969); Finn et al., The Proteins, 3rd ed., vol. 2, pp. 105-253 (1976); and Erickson et al., The Proteins, 3rd ed., vol. 2, pp. 257-527 (1976). The following descriptions of synthetic methods are designed to illustrate, but not to limit, general procedures for the preparation of compounds of the present disclosure.

The synthetic processes disclosed herein can tolerate a wide variety of functional groups; therefore, various substituted starting materials can be used. The processes generally provide the desired final compound at or near the end of the overall process, although it may be desirable in certain instances to further convert the compound to a pharmaceutically acceptable salt, ester or prodrug thereof.

In general, compounds of Formula I can be synthesized according to Schemes 1 or 2.

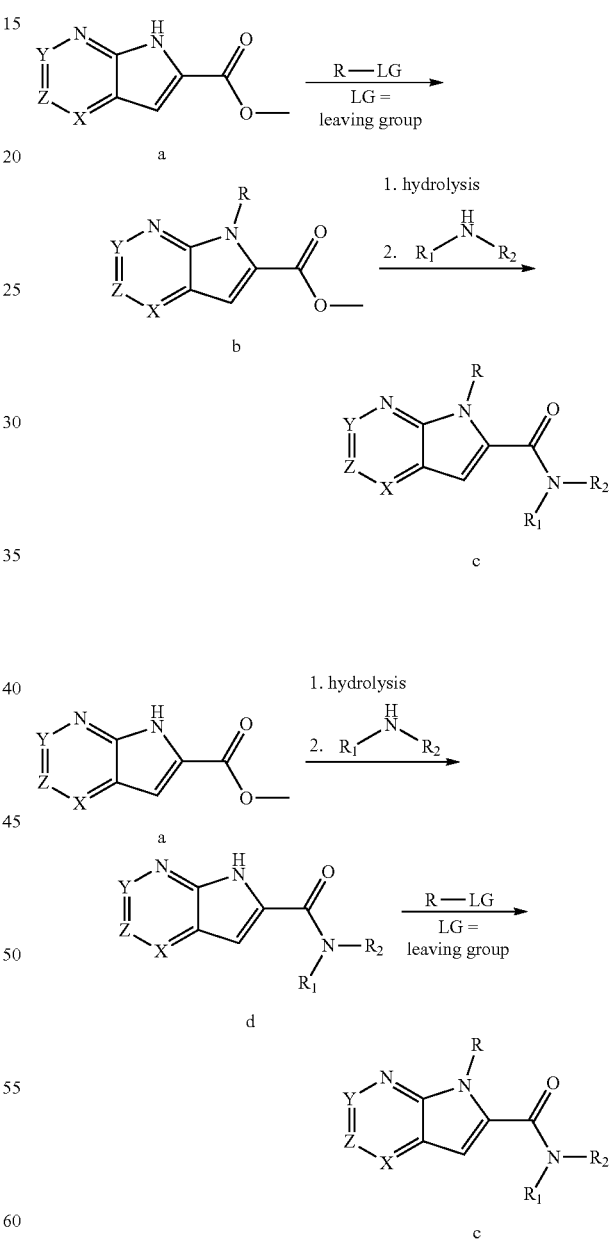

Compounds having structure c can be synthesized using the procedure shown in Schemes 1 or 2.

In Scheme 1, treatment of methyl ester a with a derivative of substituent group R comprising a leaving group, e.g., a boronic acid, and appropriate reagents, e.g., chloral hydrate, ammonium hydroxide, and concentrated sulfuric acid, produces derivative compound b. For example, in cases, where R is an aryl group, e.g., 3,4-dichlorophenyl, treatment of a with an arylboronic acid, e.g., (3,4-dichlorophenyl)boronic acid, under coupling conditions (e.g., treatment with copper (II) acetate and pyridine in dichloromethane at room temperature for 12 hours), produces a compound b where R is an aryl group, e.g., 3,4-dichlorophenyl. Hydrolysis of b under appropriate conditions, e.g., treatment with sodium hydroxide in a mixture of methanol and water, followed by treatment with an amine having a structure $NHR_1R_2$ under appropriate coupling conditions, e.g., propanephosphonic acid anhydride (T3P) and diisopropylethylamine (DI PEA) in dimethylformamide (DMF) at room temperature from 30 minutes to 4 hours, produces compounds of Formula I having structure c. Appropriate coupling conditions will be known to those skilled in the art, but are contemplated to include, without limitation, transition metal catalyzed additions such as copper catalyzed additions (e.g., a Lam coupling).

The conditions of Scheme 2 are identical to those in Scheme 1, except that the hydrolysis and amine coupling can be performed to form an amide d before coupling with the R group to form a compound of Formula I having a structure c.

Additional synthetic procedures for preparing the compounds disclosed herein can be found in the Examples section.

Pharmaceutical Formulations, Dosing, and Routes of Administration

Further provided are pharmaceutical formulations comprising a compound as described herein (e.g., compounds of Formula I or pharmaceutically acceptable salts of the compounds) and a pharmaceutically acceptable excipient.

The compounds described herein can be administered to a subject in a therapeutically effective amount (e.g., in an amount sufficient to prevent or relieve the symptoms of a disorder associated with aberrant PDE4 activity). The compounds can be administered alone or as part of a pharmaceutically acceptable composition or formulation. In addition, the compounds can be administered all at once, multiple times, or delivered substantially uniformly over a period of time. It is also noted that the dose of the compound can be varied over time.

A particular administration regimen for a particular subject will depend, in part, upon the compound, the amount of compound administered, the route of administration, and the cause and extent of any side effects. The amount of compound administered to a subject (e.g., a mammal, such as a human) in accordance with the disclosure should be sufficient to effect the desired response over a reasonable time frame. Dosage typically depends upon the route, timing, and frequency of administration. Accordingly, the clinician titers the dosage and modifies the route of administration to obtain the optimal therapeutic effect, and conventional range-finding techniques are known to those of ordinary skill in the art.

Purely by way of illustration, the method comprises administering, e.g., from about 0.1 mg/kg up to about 100 mg/kg of compound or more, depending on the factors mentioned above. In other embodiments, the dosage ranges from 1 mg/kg up to about 100 mg/kg; or 5 mg/kg up to about 100 mg/kg; or 10 mg/kg up to about 100 mg/kg. Some conditions require prolonged treatment, which may or may not entail administering lower doses of compound over multiple administrations. If desired, a dose of the compound is administered as two, three, four, five, six or more sub-doses administered separately at appropriate intervals throughout the day, optionally, in unit dosage forms. The treatment period will depend on the particular condition, and may last one day to several months.

Suitable methods of administering a physiologically-acceptable composition, such as a pharmaceutical composition comprising the compounds disclosed herein (e.g., compounds of Formula I), are well known in the art. Although more than one route can be used to administer a compound, a particular route can provide a more immediate and more effective reaction than another route. Depending on the circumstances, a pharmaceutical composition comprising the compound is applied or instilled into body cavities, absorbed through the skin or mucous membranes, ingested, inhaled, and/or introduced into circulation. For example, in certain circumstances, it will be desirable to deliver a pharmaceutical composition comprising the agent orally, through injection by intravenous, intraperitoneal, intracerebral (intra-parenchymal), intracerebroventricular, intramuscular, intra-ocular, intraarterial, intraportal, intralesional, intramedullary, intrathecal, intraventricular, transdermal, subcutaneous, intraperitoneal, intranasal, enteral, topical, sublingual, urethral, vaginal, or rectal means, by sustained release systems, or by implantation devices. If desired, the compound is administered regionally via intrathecal administration, intracerebral (intra-parenchymal) administration, intracerebroventricular administration, or intraarterial or intravenous administration feeding the region of interest. Alternatively, the composition is administered locally via implantation of a membrane, sponge, or another appropriate material onto which the desired compound has been absorbed or encapsulated. Where an implantation device is used, the device is, in one aspect, implanted into any suitable tissue or organ, and delivery of the desired compound is, for example, via diffusion, timed-release bolus, or continuous administration.

To facilitate administration, the compound is, in various aspects, formulated into a physiologically-acceptable composition comprising a carrier (e.g., vehicle, adjuvant, or diluent). The particular carrier employed is limited only by chemico-physical considerations, such as solubility and lack of reactivity with the compound, and by the route of administration. Physiologically-acceptable carriers are well known in the art. Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). Injectable formulations are further described in, e.g., Pharmaceutics and Pharmacy Practice, J. B. Lippincott Co., Philadelphia. Pa., Banker and Chalmers, eds., pages 238-250 (1982), and ASHP Handbook on Injectable Drugs, Toissel, 4th ed., pages 622-630 (1986)). A pharmaceutical composition comprising the compound is, in one aspect, placed within containers, along with packaging material that provides instructions regarding the use of such pharmaceutical compositions. Generally, such instructions include a tangible expression describing the reagent concentration, as well as, in certain embodiments, relative amounts of excipient ingredients or diluents (e.g., water, saline or PBS) that may be necessary to reconstitute the pharmaceutical composition.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. The solid dosage forms may also contain opacifying agents. Further, the solid dosage forms may be embedding compositions, such that they release the active compound or compounds in a certain part of the intestinal tract in a delayed manner. Examples of embedding compositions that can be used are polymeric substances and waxes. The active compound can also be in micro-encapsulated form, optionally with one or more excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

In a particular example, a compound or mixture is administered orally, such as by mixing with distilled water. In another example, a test compound or mixture is administered intravenously, such as in saline or distilled water. In some examples, treatment with test compound may be a single dose or repeated doses. The test compound may be administered about every 6 hours, about every 12 hours, about every 24 hours (daily), about every 48 hours, about every 72 hours, or about weekly. Treatment with repeated doses may continue for a period of time, for example for about 1 week to 12 months, such as about 1 week to about 6 months, or about 2 weeks to about 3 months, or about 1 to 2 months. Administration of a compound may also continue indefinitely. Doses of test compound are from about 0.1 mg/kg to about 400 mg/kg, such as about 1 mg/kg to about 300 mg/kg, about 2 mg/kg to 200 mg/kg, about 10 mg/kg to about 100 mg/kg, about 20 mg/kg to about 75 mg/kg, or about 25 mg/kg to about 50 mg/kg.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration can be suppositories, which can be prepared by mixing the compounds of the disclosure with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

The compositions used in the methods of the invention may be formulated in micelles or liposomes. Such formulations include sterically stabilized micelles or liposomes and sterically stabilized mixed micelles or liposomes. Such formulations can facilitate intracellular delivery, since lipid bilayers of liposomes and micelles are known to fuse with the plasma membrane of cells and deliver entrapped contents into the intracellular compartment.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

The frequency of dosing will depend on the pharmacokinetic parameters of the agents and the routes of administration. The optimal pharmaceutical formulation will be determined by one of skill in the art depending on the route of administration and the desired dosage. See, for example, Remington's Pharmaceutical Sciences, 18th Ed. (1990) Mack Publishing Co., Easton, Pa., pages 1435-1712, incorporated herein by reference. Such formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein, as well as the pharmacokinetic data observed in animals or human clinical trials.

The precise dosage to be employed depends upon several factors including the host, whether in veterinary medicine or human medicine, the nature and severity of the condition, e.g., disease or disorder, being treated, the mode of administration and the particular active substance employed. The compounds may be administered by any conventional route, in particular enterally, and, in one aspect, orally in the form of tablets or capsules. Administered compounds can be in the free form or pharmaceutically acceptable salt form as appropriate, for use as a pharmaceutical, particularly for use in the prophylactic or curative treatment of a disease of interest. These measures will slow the rate of progress of the disease state and assist the body in reversing the process direction in a natural manner.

It will be appreciated that the pharmaceutical compositions and treatment methods of the invention are useful in fields of human medicine and veterinary medicine. Thus the subject to be treated is in one aspect a mammal. In another aspect, the mammal is a human.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

Methods of Use

As such, the compounds described herein modulate PDE4A, PDE4B, or PDE4D, e.g., the compounds trigger or inhibit PDE4A, PDE4B, or PDE4D-mediated biological activity, such as regulating the intracellular concentrations of cAMP. In various embodiments, the compounds are PDE4 inhibitors, e.g., the compounds change, inhibit, or prevent one or more biological activities mediated by PDE4. In some embodiments, the compounds show enhanced selectivity for one isoform of PDE4 over other isoforms of PDE4. In some embodiments, the compounds are selective for PDE4B and/or PDE4D. In some embodiments, the compounds are selective for PDE4B over the other PDE4 isoforms. In some embodiments, the compounds are selective for PDE4D over the other PDE4 isoforms.

The compounds disclosed herein are particularly advantageous for the treatment of diseases or disorders caused by aberrant expression or activity of PDE4. The incidence and/or intensity of diseases or disorders associated with aberrant expression or activity of PDE4 can be reduced by administration of a compound disclosed herein.

Aberrant expression or activity of PDE4 is associated with many adverse conditions. These include, for example, cancer, neurodegenerative diseases (e.g., Alzheimer's disease, Parkinson's disease, or ALS), multiple sclerosis, Chronic Traumatic Encephalopathy (CTE), Traumatic Brain Injury (TBI), Batten Disease (including but not limited to CLN1 disease infantile onset, CLN1 disease juvenile onset, CLN2 disease late infantile onset, CLN2 disease later onset, CLN3 disease juvenile onset, CLN4 disease adult onset, CLN5 disease variant late-infantile onset, CLN6 disease variant late-infantile onset, CLN6 disease adult onset, CLN7 disease variant late-infantile onset, CLN8 disease, or CLN10 disease), addiction, autoimmune disorders, inflammatory disorders, chronic obstructive pulmonary disease (COPD), depression and depressive disorders, anxiety disorders, schizophrenia, attention deficit-hyperactivity disorder, asthma, rheumatoid arthritis, stroke, autism, Huntington's disease, atopic dermatitis, psoriatic arthritis, and plaque psoriasis.

Cancers contemplated in the disclosed methods of use include but are not limited to ovarian cancer, breast cancer, prostate cancer, colon cancer, liver cancer, brain cancer, kidney cancer, lung cancer, leukemia, lymphoma, multiple myeloma, thyroid cancer, bone cancer, esophageal cancer, and pancreatic cancer.

Compounds of Formula I and as disclosed in Table A display high selectivity for PDE4 inhibition (e.g., PDE4B inhibition) and/or inhibition of macrophage pro-inflammatory activity. As such, compounds as disclosed herein are useful as therapeutics in inflammatory diseases. Inflammatory diseases contemplated in the disclosed methods of use include but are not limited to arthritis, rheumatoid arthritis, atherosclerosis, multiple sclerosis, asthma, inflammatory bowel disease, Crohn's disease, gastritis, pancreatitis, systemic inflammatory response syndrome, and chronic inflammatory demyelinating polyradiculoneuritis. In some cases, the compounds described herein can be used to decrease or prevent inflammatory diseases in human subjects with e.g., chronic obstructive pulmonary disorder (COPD), asthma, rheumatoid arthritis, psoriasis, or psoriatic arthritis.

Addictions contemplated in the disclosed methods of use include but are not limited to cocaine addiction, methamphetamine addiction, heroin addiction, and alcohol addiction. In some embodiments, the addiction is cocaine addiction.

PDE4 selective inhibitors have been used previously for several disease states, e.g., as a therapeutic strategy in the treatment of COPD and psoriatic arthritis. However, PDE4 inhibitor therapy has been hampered by dose-limiting side effects such as nausea and emesis. These side effects are hypothesized to be partially associated with the inhibition of PDE4D isoform. Selective inhibition of PDE4 isoforms other than PDE4D (e.g., selective inhibition of PDE4B) can be a useful strategy for treating or preventing inflammatory diseases with fewer or no dose-limiting side effects.

The disclosed methods include methods for treating diseases or disorders capable of being modulated by inhibition of PDE4, e.g., inflammatory diseases or addiction, comprising administering to a subject a compound that inhibits PDE4. In some examples, the methods disclosed herein comprise use of a compound that reduces production of TNFα. Also provided herein are methods of modulating PDE4 (e.g., PDE4B and/or PDE4D, in particular PDE4B) in a cell. In some embodiments, the methods involve contacting a cell with a compound disclosed herein (e.g., a compound of Formula I or as shown in Table A). The contacting of the cell can occur in vitro or in vivo. In some cases, contacting of the cell occurs in vitro. In other cases, contacting of the cell occurs in vivo. Therefore, the disclosure includes administering one or more of a compound described herein to a subject, such as a human, in need thereof. In some embodiments, the subject suffers from a disease or disorder associated with aberrant activity of PDE4, as discussed above.

It will be understood that the methods and compositions described herein for treating cancer, comprising administering a compound that inhibits PDE4, are applicable to methods of treating other diseases related to PDE4 activity, such as those described above. The methods for assessing the effectiveness of test compounds for treating such diseases in cells, appropriate animal models, or affected subjects are known to one of skill in the art.

Uses of the compounds disclosed herein in the preparation of a medicament for treating diseases or disorders related to PDE4 activity also are provided herein.

The disclosure herein will be understood more readily by reference to the following examples, below.

EXAMPLES

The following examples are provided for illustration and are not intended to limit the scope of the disclosure.

Synthetic Procedures for Compounds of Formula I

General Experimental Procedures. All reagents were purchased from commercial sources and were used without further purification.

Example 1: Compounds of Formula (I)

General Reaction Scheme for Compounds 1-15:

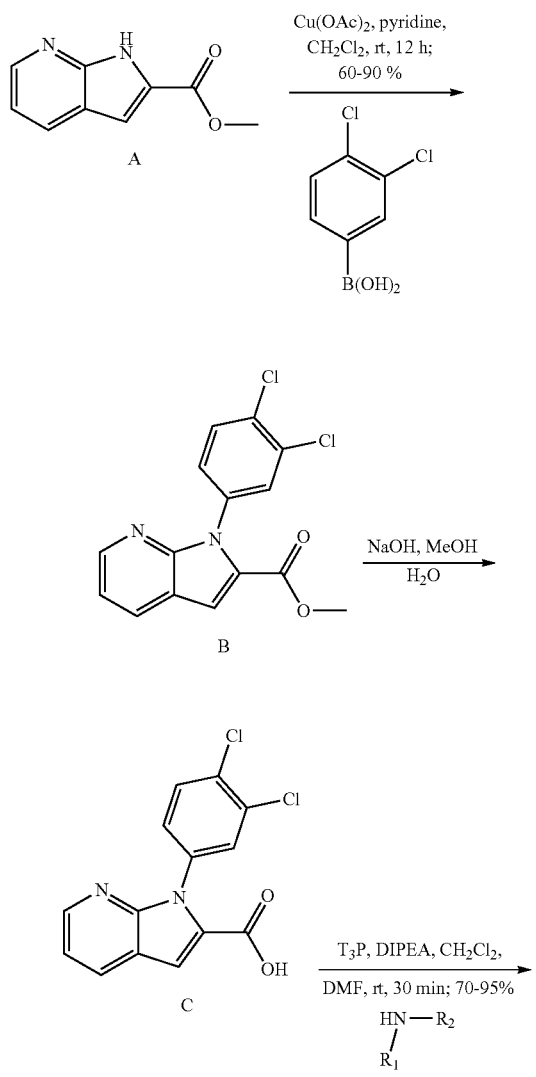

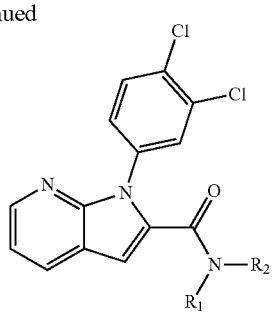

Methyl 1-(3,4-dichlorophenyl)-1H-pyrrolo[2,3-b]pyridine-2-carboxylate (B). A reaction flask was charged with A (0.055 g; 0.27 mmol), 3-chloro-4-methylphenyl boronic acid (0.093 g; 0.54 mmol), cupric acetate (0.074 g; 0.41 mmol), $CH_2Cl_2$ (5 mL) and then pyridine (0.088 mL; 1.1 mmol). The reaction mixture was stirred at room temperature overnight. The mixture was filtered through a short pad of Celite. The filtrate was concentrated and purified on silica gel (eluting with 0-50% EtOAc/hexane followed by 0-5% MeOH/dichloromethane) to give the desired product. LCMS: $R_T$=2.92 min, >98% @ 215 and 254 nm, m/z=321.0 [M+H]$^+$; $^1$H NMR (499 MHz, DMSO-$d_6$) δ 8.43 (d, J=4.3 Hz, 1H), 8.26 (d, J=7.8 Hz, 1H), 7.83 (s, 1H), 7.78 (d, J=8.5 Hz, 1H), 7.51 (s, 1H), 7.46 (d, J=8.9 Hz, 1H), 7.37-7.29 (m, 1H), 3.77 (s, 3H).

1-(3,4-dichlorophenyl)-1H-pyrrolo[2,3-b]pyridine-2-carboxylic acid (C). To a solution of the B (0.12 g; 0.36 mmol) in MeOH (6.0 mL) was added a predissolved solution of NaOH (0.36 mL; 0.72 mmol) in $H_2O$ (1.0 mL). The reaction mixture was stirred at rt overnight. The reaction mixture was then concentrated in vacuo and acidified with 1N HCl (pH≈4). The aq mixture was extracted with EtOAc, dried (MgSO$_4$) and concentrated to give the corresponding acid derivative which was used without further purification. LCMS: $R_T$=2.560 min, >98% @ 215 and 254 nm, m/z=306.9 [M+H]$^+$; $^1$H NMR (499 MHz, DMSO-$d_6$) δ 13.19 (s, 1H), 8.41 (d, J=4.5 Hz, 1H), 8.24 (d, J=7.9 Hz, 1H), 7.81 (d, J=2.5 Hz, 1H), 7.77 (d, J=8.5 Hz, 1H), 7.45 (q, J=3.3, 2.0 Hz, 2H), 7.30 (dd, J=8.0, 4.6 Hz, 1H).

General Amine Coupling Procedure:

A vial equipped with magnetic stir bar and screw cap vial was charged with C (0.10 g; 0.60 mmol), amine (0.44 mL; 3.1 mmol), diisopropyl ethylamine (0.047 mL; 0.67 mmol), $CH_2Cl_2$ (10.0 mL) and was stirred for approximately 5 minutes. Propylphoshonic anhydride (T$_3$P, 50 wt. % in ethyl acetate) (0.55 mL; 9.6 mmol), was added and the reaction stirred until LCMS analysis indicated significant consumption of the starting materials (30 min). The crude reaction mixture was diluted with water (15 mL) and the mixture extracted with dichloromethane (4×15 mL). The combined organic layers were dried over Na2SO$_4$ and were evaporated under reduced pressure to give the crude product that was purified by flash column chromatography on silica gel (dry loaded using silica/DCM) with a gradient of 0-100% ethyl acetate in hexanes to give the corresponding amide product 1-15.

N-cyclopropyl-1-(3,4-dichlorophenyl)-1H-pyrrolo[2,3-b] pyridine-2-carboxamide (1). LCMS: $R_T$=2.597 min, >98% @ 215 and 254 nm, m/z=346.0 [M+H]$^+$; $^1$H NMR (499 MHz, CDCl$_3$) δ 8.44 (d, J=4.7 Hz, 1H), 8.02 (d, J=7.8 Hz, 1H), 7.67-7.48 (m, 2H), 7.33 (d, J=8.5 Hz, 1H), 7.21 (dd, J=7.8, 4.3 Hz, 1H), 6.97 (s, 1H), 6.25 (s, 1H), 2.82 (dq, J=7.4, 4.0 Hz, 1H), 0.86 (d, J=6.8 Hz, 2H), 0.62-0.51 (m, 2H). $^{13}$C NMR (126 MHz, CDCl$_3$) δ 162.16, 149.59, 146.62, 136.16, 133.04, 132.85, 132.42, 130.58, 129.80, 127.28, 119.07, 118.10, 104.54, 22.85, 6.93.

N-cyclobutyl-1-(3,4-dichlorophenyl)-1H-pyrrolo[2,3-b]pyridine-2-carboxamide (2). LCMS: R$_T$=2.771, >98% @ 215 and 254 nm, m/z=360.0 [M+H]$^+$; $^1$H NMR (499 MHz, CDCl$_3$) δ 8.40 (t, J=12.9 Hz, 1H), 8.03 (d, J=7.8 Hz, 1H), 7.57 (d, J=8.5 Hz, 1H), 7.52 (d, J=14.7 Hz, 1H), 7.30 (d, J=8.1 Hz, 1H), 7.20 (dd, J=7.5, 4.7 Hz, 1H), 7.05 (d, J=23.5 Hz, 1H), 4.46-4.38 (m, 1H), 2.35 (d, J=8.0 Hz, 2H), 1.94-1.84 (m, 2H), 1.74 (dd, J=11.1, 5.2 Hz, 2H). $^{13}$C NMR (126 MHz, CDCl$_3$) δ 159.98, 149.12, 146.04, 136.05, 133.42, 132.78, 132.36, 130.96, 130.57, 129.67, 127.20, 118.01, 104.66, 44.84, 30.89, 15.13.

1-(3,4-Dichlorophenyl)-N-(3-fluorocyclobutyl)-1H-pyrrolo[2,3-b]pyridine-2-carboxamide (3). LCMS: R$_T$=2.696 min, >98% @ 215 and 254 nm, m/z=378.0 [M+H]$^+$; $^1$H NMR (499 MHz, CDCl$_3$) δ 8.51-8.37 (m, 1H), 8.05 (dd, J=8.2, 1.6 Hz, 1H), 7.62 (d, J=8.4 Hz, 1H), 7.56 (d, J=2.4 Hz, 1H), 7.34 (dd, J=8.4, 2.4 Hz, 1H), 7.23 (dd, J=7.9, 4.6 Hz, 1H), 7.03 (s, 1H), 6.19 (s, 1H), 5.22 (ddt, J=55.9, 6.5, 3.1 Hz, 1H), 4.64 (dt, J=8.6, 6.0 Hz, 1H), 2.72 (dddt, J=17.8, 12.0, 8.2, 3.7 Hz, 2H), 2.39 (ddt, J=20.4, 13.4, 6.0 Hz, 2H). $^{13}$C NMR (126 MHz, CDCl$_3$) δ 160.55, 149.64, 146.82, 136.06, 132.95, 132.54, 130.64, 130.62, 129.75, 127.21, 118.99, 118.20, 104.82, 87.23, 85.63, 41.77, 38.30, 38.12.

1-(3,4-dichlorophenyl)-N-(3,3-difluorocyclobutyl)-1H-pyrrolo[2,3-b]pyridine-2-carboxamide (4). LCMS: R$_T$=2.777 min, >98% @ 215 and 254 nm, m/z=396.0 [M+H]$^+$; $^1$H NMR (499 MHz, CDCl$_3$) δ 8.46 (dd, J=4.5, 1.6 Hz, 1H), 8.06 (dd, J=7.9, 1.7 Hz, 1H), 7.62 (d, J=8.4 Hz, 1H), 7.55 (d, J=2.3 Hz, 1H), 7.33 (dd, J=8.3, 2.3 Hz, 1H), 7.24 (dd, J=7.9, 4.6 Hz, 1H), 7.07 (s, 1H), 6.40-6.24 (m, 1H), 4.40 (td, J=7.6, 6.7, 3.7 Hz, 1H), 3.09 (ddt, J=11.7, 8.5, 2.9 Hz, 2H), 2.63-2.44 (m, 2H). $^{13}$C NMR (126 MHz, CDCl$_3$) δ 160.70, 149.68, 146.98, 135.98, 133.00, 132.68, 132.30, 130.78, 130.78, 130.67, 129.81, 127.27, 118.95, 118.27, 105.09, 53.43, 43.33, 43.14, 42.96, 35.36, 35.29, 35.24, 35.17.

1-(3,4-dichlorophenyl)-N-(furan-2-ylmethyl)-1H-pyrrolo[2,3-b]pyridine-2-carboxamide (5). LCMS: R$_T$=2.744 min, >98% @ 215 and 254 nm, m/z=386.0 [M+H]$^+$; $^1$H NMR (499 MHz, CDCl$_3$) δ 8.43 (dd, J=4.7, 1.6 Hz, 1H), 8.00 (dt, J=8.1, 1.3 Hz, 1H), 7.64-7.49 (m, 2H), 7.29 (dd, J=8.6, 2.4 Hz, 1H), 7.20 (dd, J=7.9, 4.7 Hz, 1H), 7.02 (s, 1H), 6.60 (dd, J=5.6 Hz, 1H), 6.38-6.28 (m, 1H), 6.24 (d, J=3.2 Hz, 1H), 4.54 (d, J=5.6 Hz, 2H). 130 NMR (126 MHz, CDCl$_3$) δ 160.62, 150.54, 149.65, 146.71, 142.42, 136.12, 132.86, 132.81, 132.33, 130.63, 130.55, 129.72, 127.19, 119.06, 118.13, 110.57, 107.88, 105.09, 36.61.

Azetidin-1-yl(1-(3,4-dichlorophenyl)-1H-pyrrolo[2,3-b]pyridin-2-yl)methanone (6). LCMS: R$_T$=2.631 min, >98% @ 215 and 254 nm, m/z=346.0 [M+H]$^+$; $^1$H NMR (499 MHz, CDCl$_3$) δ 8.44 (dd, J=4.6, 1.5 Hz, 1H), 8.04 (dd, J=7.9, 1.6 Hz, 1H), 7.67-7.52 (m, 2H), 7.34 (dd, J=8.5, 2.4 Hz, 1H), 7.22 (dd, J=7.9, 4.7 Hz, 1H), 6.89 (s, 1H), 4.50-4.10 (m, 5H), 2.39 (p, J=7.8 Hz, 2H). $^{13}$C NMR (126 MHz, CDCl$_3$) δ 161.83, 149.11, 146.36, 136.42, 132.71, 132.08, 130.94, 130.46, 130.44, 129.47, 126.99, 119.32, 117.93, 105.51, 16.05.

(1-(3,4-dichlorophenyl)-1H-pyrrolo[2,3-b]pyridin-2-yl)(3-fluoroazetidin-1-yl)methanone (7). LCMS: R$_T$=2.636, >98% @ 215 and 254 nm, m/z=364.0 [M+H]$^+$; $^1$H NMR (499 MHz, CDCl$_3$) δ 8.46 (dd, J=4.6 Hz, 1H), 8.06 (dd, J=7.8, 1.7 Hz, 1H), 7.71-7.53 (m, 2H), 7.32 (dd, J=8.4, 2.4 Hz, 1H), 7.23 (dd, J=7.9, 4.7 Hz, 1H), 6.91 (s, 1H), 5.40 (ddq, J=56.6, 6.7, 3.4 Hz, 1H), 4.52 (d, J=37.9 Hz, 4H). $^{13}$C NMR (126 MHz, CDCl$_3$) δ 162.08, 149.34, 146.91, 136.23, 132.79, 132.31, 130.62, 130.51, 130.16, 129.60, 127.09, 119.09, 118.15, 106.18, 82.84, 81.21, 29.72.

(1-(3,4-dichlorophenyl)-1H-pyrrolo[2,3-b]pyridin-2-yl)(3,3-difluoroazetidin-1-yl)methanone (8). LCMS: R$_T$=2.764 min, >98% @ 215 and 254 nm, m/z=382.0 [M+H]$^+$; $^1$H NMR (499 MHz, CDCl$_3$) δ 8.48 (dd, J=4.8, 1.6 Hz, 1H), 8.07 (dd, J=7.9, 1.6 Hz, 1H), 7.67-7.52 (m, 2H), 7.36-7.21 (m, 2H), 6.93 (s, 1H), 4.58 (s, 4H). $^{13}$C NMR (126 MHz, CDCl$_3$) δ 162.13, 162.10, 162.07, 149.48, 147.34, 136.08, 132.85, 132.49, 130.81, 130.55, 129.73, 129.51, 127.17, 118.94, 118.33, 117.35, 115.17, 112.98, 106.75.

(1-(3,4-dichlorophenyl)-1H-pyrrolo[2,3-b]pyridin-2-yl)(3,3-difluoroazetidin-1-yl)methanone (9). LCMS: R$_T$=2.830 min, >98% @ 215 and 254 nm, m/z=414.0 [M+H]$^+$; $^1$H NMR (499 MHz, CDCl$_3$) δ 8.46 (dd, J=4.6, 1.7 Hz, 1H), 8.05 (dd, J=7.9, 1.7 Hz, 1H), 7.64-7.54 (m, 2H), 7.38-7.27 (m, 1H), 7.23 (dd, J=7.9, 4.7 Hz, 1H), 6.92 (s, 1H), 4.61-4.14 (m, 4H), 3.37 (dtd, J=14.1, 8.7, 5.3 Hz, 1H). $^{13}$C NMR (126 MHz, CDCl$_3$) δ 162.11, 149.31, 146.98, 136.14, 132.81, 132.29, 130.70, 130.53, 129.64, 129.52, 127.00, 119.10, 118.23, 106.25, 51.89, 48.00, 32.98, 32.73, 32.47, 32.21.

(1-(3,4-dichlorophenyl)-1H-pyrrolo[2,3-b]pyridin-2-yl)(1-oxa-6-azaspiro[3.5]nonan-6-yl)methanone (10). LCMS: R$_T$=2.685 min, >98% @ 215 and 254 nm, m/z=416.0 [M+H]$^+$; $^1$H NMR (499 MHz, CDCl$_3$) δ 8.52-8.36 (m, 1H), 8.03 (d, J=7.7 Hz, 1H), 7.75 (d, J=90.1 Hz, 1H), 7.64-7.40 (m, 2H), 7.22 (dd, J=7.9, 4.7 Hz, 1H), 6.80 (dd, J=30.8, 9.8 Hz, 1H), 4.79-4.44 (m, 2H), 4.45-4.06 (m, 2H), 3.42 (ddd, J=60.5, 22.2, 10.6 Hz, 2H), 3.26-2.95 (m, 1H), 2.50-2.20 (m, 2H), 2.07-1.53 (m, 4H). $^{13}$C NMR (126 MHz, CDCl$_3$) b 162.47, 145.52, 135.72, 132.96, 131.63, 130.72, 130.10, 128.47, 126.00, 119.63, 117.94, 104.13, 103.45, 82.26, 65.27, 64.56, 56.68, 36.48, 30.20, 20.67.

(1-(3,4-dichlorophenyl)-1H-pyrrolo[2,3-b]pyridin-2-yl)(1,1-dioxidothiomorpholino) methanone (11). LCMS: R$_T$=2.505 min, >98% @ 215 and 254 nm, m/z=424.0 [M+H]$^+$; $^1$H NMR (499 MHz, DMSO-d$_6$) δ 8.40 (dd, J=4.6, 1.6 Hz, 1H), 8.20 (dd, J=7.9, 1.6 Hz, 1H), 7.89 (d, J=2.4 Hz, 1H), 7.78 (d, J=8.6 Hz, 1H), 7.43 (dd, J=8.6, 2.5 Hz, 1H), 7.32 (dd, J=7.9, 4.6 Hz, 1H), 4.04 (s, 4H), 3.27 (t, J=5.3 Hz, 4H). $^{13}$C NMR (126 MHz, DMSO-d$_6$) δ 161.73, 148.39, 145.99, 136.52, 131.99, 131.51, 131.33, 131.10, 130.37, 129.71, 127.52, 119.46, 118.66, 105.00, 51.33, 40.59, 40.42, 40.26, 40.09.

(1-(3,4-dichlorophenyl)-1H-pyrrolo[2,3-b]pyridin-2-yl)(7-azaspiro[3.5]nonan-7-yl) methanone (12). LCMS: R$_T$=3.208 min, >98% @ 215 and 254 nm, m/z=414.1 [M+H]$^+$; $^1$H NMR (499 MHz, CDCl$_3$) δ 8.40 (d, J=5.3 Hz, 1H), 8.00 (d, J=7.9 Hz, 1H), 7.69 (d, J=2.4 Hz, 1H), 7.58 (d, J=8.6 Hz, 1H), 7.44 (dd, J=8.6, 2.4 Hz, 1H), 7.20 (dd, J=7.9, 4.7 Hz, 1H), 6.74 (s, 1H), 3.46 (d, J=127.2 Hz, 4H), 1.91 (q, J=7.9, 6.9 Hz, 2H), 1.78 (dt, J=16.7, 7.9 Hz, 4H), 1.59 (s, 2H), 1.37 (s, 2H). $^{13}$C NMR (126 MHz, CDCl$_3$) δ 161.84, 148.02, 145.31, 135.79, 133.52, 132.97, 131.63, 130.75, 130.04, 129.96, 128.38, 125.86, 119.76, 117.94, 103.15, 44.32, 39.18, 37.83, 36.85, 31.35, 15.01.

(1-(3,4-dichlorophenyl)-1H-pyrrolo[2,3-b]pyridin-2-yl)(6-azaspiro[3.4]octan-6-yl) methanone (13). LCMS: R$_T$=3.024 min, >98% @ 215 and 254 nm, m/z=400.0 [M+H]$^+$; $^1$H NMR (499 MHz, CDCl$_3$) δ 8.42 (t, J=4.9 Hz, 1H), 8.02 (t, J=7.9 Hz, 1H), 7.66 (d, J=2.4 Hz, 1H), 7.57 (d, J=8.5 Hz, 1H), 7.43 (dd, J=8.7, 2.4 Hz, 1H), 7.22 (dd, J=8.1, 4.5 Hz, 1H), 6.84 (d, J=9.3 Hz, 1H), 3.57 (t, J=7.1 Hz, 1H), 3.41 (d, J=2.6 Hz, 2H), 2.06-1.79 (m, 9H). $^{13}$C NMR (126 MHz, CDCl$_3$) δ 161.55, 145.66, 136.11, 134.13, 132.90, 131.62, 130.67, 130.15, 128.42, 125.92, 119.67, 117.95, 103.77, 103.71, 59.79, 57.23, 47.19, 45.12, 44.73, 43.56, 37.62, 36.02, 30.92, 30.56, 15.93.

(1-(3,4-dichlorophenyl)-1H-pyrrolo[2,3-b]pyridin-2-yl) (6-azaspiro[3.4]octan-6-yl) methanone (14). A solution of tert-butyl 2-(1-(3,4-dichlorophenyl)-1H-pyrrolo[2,3-b]pyridine-2-carbonyl)-2,7-diazaspiro[4.5]decane-7-carboxylate (0.035 g, 0.066 mmol) in CH$_2$Cl$_2$ (5.0 mL) was treated with TFA (0.65 mL) for 12 h. The solvent was removed in vacuo and the crude was dissolved in 10% MeOH/CH$_2$Cl$_2$, washed with sat. aq. NaHCO$_3$, brine, dried (MgSO$_4$), and concentrated. The crude product was purified on silica gel (eluting with 0-15% MeOH/DCM) to give the desired product Compound 14. LCMS: R$_T$=1.996 min, >98% @ 215 and 254 nm, m/z=429.1 [M+H]$^+$; $^1$H NMR (499 MHz, CDCl$_3$) δ 8.40 (dd, J=11.1, 4.7 Hz, 1H), 8.00 (d, J=7.9 Hz, 1H), 7.70-7.52 (m, 2H), 7.40 (ddd, J=25.0, 8.5, 2.5 Hz, 1H), 7.19 (td, J=8.7, 4.7 Hz, 1H), 6.88 (d, J=21.0 Hz, 1H), 4.38 (s, 3H), 3.61 (dtt, J=24.3, 15.2, 8.8 Hz, 3H), 3.40 (dd, J=33.6, 12.2 Hz, 1H), 3.14-2.64 (m, 4H), 1.95 (ddt, J=52.3, 13.5, 6.9 Hz, 1H), 1.85-1.60 (m, 2H). $^{13}$C NMR (126 MHz, CDCl$_3$) δ 148.30, 145.77, 136.21, 133.70, 132.75, 131.55, 130.70, 130.28, 128.52, 126.16, 119.51, 117.92, 104.21, 57.15, 54.89, 46.86, 44.17, 35.18, 33.79, 32.82.

(1-(3,4-dichlorophenyl)-1H-pyrrolo[2,3-b]pyridin-2-yl) (2,7-diazaspiro[3.5]nonan-2-yl) methanone (15). A solution of tert-butyl 2-(1-(3,4-dichlorophenyl)-1H-pyrrolo[2,3-b]pyridine-2-carbonyl)-2,7-diazaspiro[3.5]nonane-7-carboxylate (0.055 g, 0.087 mmol) in CH$_2$Cl$_2$ (5.0 mL) was treated with TFA (0.65 mL) for 12 h. The solvent was removed in vacuo and the crude was dissolved in 10% MeOH/CH$_2$Cl$_2$, washed with sat. aq. NaHCO$_3$, brine, dried (MgSO$_4$), and concentrated. The crude product was purified on silica gel (eluting with 0-15% MeOH/DCM) to give the desired product Compound 15. LCMS: R$_T$=1.939 min, >98% @ 215 and 254 nm, m/z=415.0 [M+H]$^+$; $^1$H NMR (499 MHz, CDCl$_3$) δ 8.43 (d, J=4.6 Hz, 1H), 8.02 (d, J=7.9 Hz, 1H), 7.67-7.51 (m, 2H), 7.33 (dd, J=8.5, 2.4 Hz, 1H), 7.20 (dd, J=8.0, 4.6 Hz, 1H), 6.90 (s, 1H), 4.01 (s, 2H), 3.84 (s, 3H), 2.88 (d, J=8.0 Hz, 4H), 1.90-1.70 (m, 4H). $^{13}$C NMR (126 MHz, CDCl$_3$) δ 162.20, 149.14, 146.62, 136.45, 132.65, 132.02, 130.63, 130.49, 130.47, 129.45, 127.00, 119.22, 118.08, 105.85, 62.70, 58.40, 50.55, 48.65, 42.61, 34.91, 34.30.

General Procedure for Compounds 16-43.

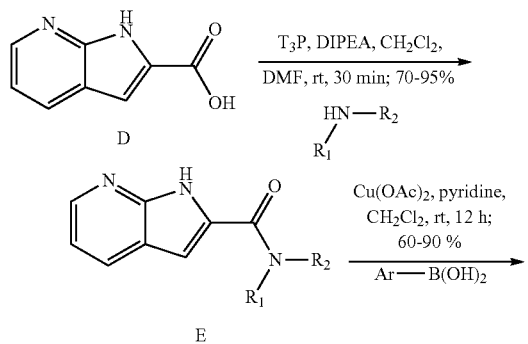

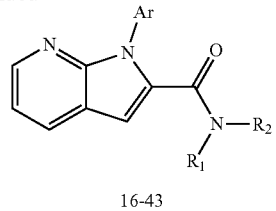

1-(3-chloro-4-methylphenyl)-N-cyclopropyl-1H-pyrrolo[2,3-b]pyridine-2-carboxamide (16). LCMS: R$_T$=1.939 min, >98% @ 215 and 254 nm, m/z=415.0 [M+H]$^+$; $^1$H NMR (499 MHz, CDCl$_3$) δ 8.46 (d, J=4.0 Hz, 1H), 8.06 (dd, J=7.8, 1.6 Hz, 1H), 7.55 (t, J=8.2 Hz, 1H), 7.33 (dd, J=9.4, 2.4 Hz, 1H), 7.22 (ddd, J=11.3, 8.4, 3.8 Hz, 2H), 6.92 (s, 1H), 5.39 (ddq, J=56.6, 6.4, 3.2 Hz, 1H), 4.68-4.16 (m, 5H). $^{13}$C NMR (126 MHz, CDCl$_3$) δ 162.12, 162.10, 158.77, 156.77, 149.26, 146.86, 136.60, 136.53, 130.64, 130.56, 130.23, 124.07, 124.04, 120.91, 120.77, 119.15, 118.17, 116.45, 116.27, 106.22, 99.98, 82.82, 81.18, 29.72.

1-(3-chloro-4-methylphenyl)-N-cyclobutyl-1H-pyrrolo[2,3-b]pyridine-2-carboxamide (17). LCMS: R$_T$=2.723 min, >98% @ 215 and 254 nm, m/z=340.0 [M+H]$^+$; 1H NMR (499 MHz, CDCl$_3$) δ 8.39 (d, J=4.2 Hz, 1H), 8.03 (d, J=7.8 Hz, 1H), 7.43 (s, 1H), 7.39 (d, J=8.0 Hz, 1H), 7.29-7.24 (m, 2H), 7.18 (dd, J=7.7, 4.8 Hz, 1H), 7.06 (s, 1H), 4.46-4.39 (m, 1H), 2.32 (m, 2H), 2.21 (s, 3H), 1.83-1.75 (m, 2H), 1.70 (dt, J=11.3, 4.6 Hz, 2H). $^{13}$C NMR (126 MHz, CDCl$_3$) δ 159.99, 149.28, 145.99, 136.51, 135.19, 134.67, 133.67, 131.27, 130.83, 128.35, 126.13, 119.32, 117.74, 104.91, 44.77, 30.92, 19.85, 15.11.

1-(4-chloro-3-methylphenyl)-N-(3-fluorocyclobutyl)-1H-pyrrolo[2,3-b]pyridine-2-carboxamide (18). LCMS: R$_T$=2.644 min, >98% @ 215 and 254 nm, m/z=358.0 [M+H]$^+$; $^1$H NMR (499 MHz, CDCl$_3$) δ 8.49-8.40 (m, 1H), 8.08-7.98 (m, 1H), 7.49-7.38 (m, 2H), 7.29 (d, J=2.2 Hz, 1H), 7.24-7.14 (m, 1H), 7.07 (s, 1H), 6.08 (d, J=6.2 Hz, 1H), 5.13 (dq, J=56.1, 4.0, 2.5 Hz, 1H), 4.65-4.53 (m, 1H), 2.75-2.58 (m, 2H), 2.47 (s, 3H), 2.28 (td, J=14.0, 7.0 Hz, 2H). $^{13}$C NMR (126 MHz, CDCl$_3$) δ 160.58, 146.51, 141.19, 136.62, 135.93, 135.21, 134.83, 133.81, 131.39, 130.73, 128.45, 126.18, 117.90, 105.27, 41.50, 38.27, 38.09, 20.60, 19.94.

(1-(3-chloro-4-methylphenyl)-1H-pyrrolo[2,3-b]pyridin-2-yl)(3-fluoroazetidin-1-yl) methanone (20). LCMS: R$_T$=2.588 min, >98% @ 215 and 254 nm, m/z=344.0 [M+H]$^+$; $^1$H NMR (499 MHz, CDCl$_3$) δ 8.46 (s, 1H), 8.05 (d, J=8.0 Hz, 1H), 7.47 (s, 1H), 7.39 (d, J=7.9 Hz, 1H), 7.27 (s, 1H), 7.22 (d, J=7.1 Hz, 1H), 6.90 (s, 1H), 5.37 (dtt, J=56.5, 6.4, 3.5 Hz, 1H), 4.40 (d, J=89.2 Hz, 5H), 2.46 (s, 3H). $^{13}$C NMR (126 MHz, CDCl$_3$) δ 162.43, 146.71, 136.08, 135.47, 134.44, 131.07, 130.57, 130.42, 128.02, 125.80, 119.07, 117.83, 105.63, 82.85, 81.21, 29.71, 19.93.

1-(4-chloro-3,5-difluorophenyl)-N-cyclopropyl-1H-pyrrolo[2,3-b]pyridine-2-carboxamide (21). LCMS: R$_T$=2.572 min, >98% @ 215 and 254 nm, m/z=348.0 [M+H]$^+$; $^1$H NMR (499 MHz, CDCl$_3$) δ 8.50-8.38 (m, 1H), 8.02 (dd, J=7.7, 1.6 Hz, 1H), 7.23 (dd, J=7.9, 4.6 Hz, 1H), 7.17-7.07 (m, 2H), 6.95 (s, 1H), 6.33 (s, 1H), 2.84 (dq, J=7.2, 3.6 Hz, 1H), 0.88 (d, J=6.8 Hz, 2H), 0.66-0.57 (m, 2H). $^{13}$C NMR (126 MHz, CDCl$_3$) δ 162.02, 159.60, 159.57, 157.61, 157.57, 149.54, 146.80, 136.31, 132.68, 130.65, 119.06, 118.32, 112.40, 112.21, 104.65, 22.88, 6.91.

1-(4-chloro-3,5-difluorophenyl)-N-cyclobutyl-1H-pyrrolo[2,3-b]pyridine-2-carboxamide (22). LCMS: R$_T$=2.742 min, >98% @ 215 and 254 nm, m/z=362.0 [M+H]⁺; ¹H NMR (499 MHz, CDCl₃) δ 8.45 (s, 1H), 8.04 (d, J=7.8 Hz, 1H), 7.24 (dd, J=7.6, 4.6 Hz, 1H), 7.14 (d, J=7.4 Hz, 2H), 7.00 (s, 1H), 6.28 (d, J=6.3 Hz, 1H), 4.56-4.45 (m, 1H), 2.47-2.39 (m, 2H), 2.00-1.91 (m, 3H), 1.83-1.76 (m, 2H). ¹³C NMR (126 MHz, CDCl₃) δ 159.67, 159.61, 159.57, 157.61, 157.57, 149.37, 146.54, 136.25, 133.18, 130.72, 118.31, 112.33, 112.12, 104.59, 45.05, 31.18, 15.18.

(1-(4-chloro-3,5-difluorophenyl)-1H-pyrrolo[2,3-b]pyridin-2-yl)(3-fluoroazetidin-1-yl) methanone (25). LCMS: R$_T$=2.611 min, >98% @ 215 and 254 nm, m/z=366.0 [M+H]⁺; ¹H NMR (499 MHz, CDCl₃) δ 8.47 (dd, J=4.7, 1.6 Hz, 1H), 8.06 (dd, J=7.9, 1.6 Hz, 1H), 7.25 (dd, J=8.0, 4.7 Hz, 1H), 7.20-7.08 (m, 2H), 6.92 (s, 1H), 5.43 (dtt, J=56.4, 6.3, 3.4 Hz, 1H), 4.50 (s, 4H). ¹³C NMR (126 MHz, CDCl₃) δ 161.74, 159.58, 159.54, 157.58, 157.54, 149.22, 147.04, 136.42, 136.32, 130.78, 129.97, 119.15, 118.39, 112.24, 112.22, 112.19, 112.07, 112.04, 112.02, 106.63, 82.82, 81.18, 29.71.

1-(4-cyano-3,5-difluorophenyl)-N-cyclopropyl-1H-pyrrolo[2,3-b]pyridine-2-carboxamide (26). LCMS: R$_T$=2.444 min, >98% @ 215 and 254 nm, m/z=339.0 [M+H]⁺; ¹H NMR (499 MHz, CDCl₃) δ 8.52-8.40 (m, 1H), 8.06 (d, J=7.6 Hz, 1H), 7.28 (s, 3H), 7.23 (d, J=9.0 Hz, 1H), 7.00 (s, 1H), 6.41 (s, 1H), 2.87 (s, 1H), 0.92 (d, J=6.8 Hz, 2H), 0.75-0.59 (m, 2H). ¹³C NMR (126 MHz, CDCl₃) δ 163.89, 161.88, 149.27, 147.02, 132.49, 130.94, 119.34, 118.93, 112.10, 111.92, 109.02, 105.95, 22.99, 6.97.

1-(4-cyano-3,5-difluorophenyl)-N-cyclobutyl-1H-pyrrolo[2,3-b]pyridine-2-carboxamide (27). LCMS: R$_T$=2.612 min, >98% @ 215 and 254 nm, m/z=353.0 [M+H]⁺; ¹H NMR (499 MHz, CDCl₃) δ 8.45 (d, J=4.1 Hz, 1H), 8.08 (dd, J=19.3, 7.8 Hz, 1H), 7.30-7.26 (m, 1H), 7.23 (d, J=8.5 Hz, 2H), 7.04 (s, 1H), 6.41 (s, 1H), 4.50 (dt, J=15.8, 7.9 Hz, 1H), 2.54-2.38 (m, 2H), 2.08-1.97 (m, 2H), 1.81 (dt, J=18.2, 8.9 Hz, 3H). ¹³C NMR (126 MHz, CDCl₃) δ 163.88, 161.80, 159.52, 149.11, 146.78, 143.29, 132.86, 130.99, 119.47, 118.90, 111.95, 111.80, 109.05, 105.85, 45.18, 31.14, 15.21.

1-(4-cyano-3,5-difluorophenyl)-N-(3-fluorocyclobutyl)-1H-pyrrolo[2,3-b]pyridine-2-carboxamide (28). LCMS: R$_T$=2.542 min, >98% @ 215 and 254 nm, m/z=371.1 [M+H]⁺; ¹H NMR (499 MHz, DMSO-d₆) δ 9.08 (d, J=6.9 Hz, 1H), 8.41 (d, J=4.5 Hz, 1H), 8.26 (d, J=7.8 Hz, 1H), 7.63 (d, J=9.6 Hz, 2H), 7.41 (s, 1H), 7.34 (dd, J=7.9, 4.7 Hz, 1H), 5.29 (dddd, J=56.7, 10.3, 6.4, 4.0 Hz, 1H), 4.44 (dtd, J=11.4, 7.2, 5.7, 2.9 Hz, 1H), 4.05 (s, 4H). ¹³C NMR (126 MHz, DMSO-d₆) δ 163.25, 163.20, 161.22, 161.16, 160.16, 160.07, 149.13, 146.67, 144.69, 133.35, 131.61, 119.61, 119.21, 113.05, 112.85, 109.91, 107.09, 89.88, 88.12, 86.54, 48.19, 48.02, 47.85, 40.99, 37.77, 37.60, 31.11.

1-(4-cyano-3,5-difluorophenyl)-N-(3,3-difluorocyclobutyl)-1H-pyrrolo[2,3-b]pyridine-2-carboxamide (29). LCMS: R$_T$=2.623 min, >98% @ 215 and 254 nm, m/z=389.0 [M+H]⁺; ¹H NMR (499 MHz, CDCl₃) δ 8.49 (s, 1H), 8.09 (d, J=7.8 Hz, 1H), 7.36-7.29 (m, 1H), 7.22 (d, J=8.7 Hz, 2H), 7.11 (s, 1H), 6.59-6.38 (m, 1H), 4.42 (d, J=9.8 Hz, 1H), 3.24-3.00 (m, 2H), 2.63 (td, J=13.7, 5.9 Hz, 2H). 163.94, 161.86, 160.42, 149.37, 143.20, 131.81, 131.12, 119.14, 112.11, 111.93, 108.98, 106.57, 43.29, 43.11, 42.92, 35.58, 35.51, 35.46, 35.39.

2,6-difluoro-4-(2-(3-fluoroazetidine-1-carbonyl)-1H-pyrrolo[2,3-b]pyridin-1-yl)benzonitrile (30). LCMS: R$_T$=2.490 min, >98% @ 215 and 254 nm, m/z=357.0 [M+H]⁺; ¹H NMR (499 MHz, CDCl₃) δ 8.47 (dd, J=4.9, 1.6 Hz, 1H), 8.08 (dd, J=8.0, 1.6 Hz, 1H), 7.36-7.26 (m, 1H), 7.26-7.20 (m, 2H), 6.97 (s, 1H), 5.46 (ddt, J=56.3, 6.1, 2.9 Hz, 1H), 4.82-4.20 (m, 3H). ¹³C NMR (126 MHz, CDCl₃) δ 163.90, 163.85, 161.82, 161.77, 161.29, 161.27, 148.97, 147.25, 143.35, 131.07, 129.65, 119.43, 118.97, 112.00, 111.97, 111.83, 111.80, 109.00, 107.94, 91.41, 82.80, 81.16, 29.72.

1-(4-chlorophenyl)-N-cyclopropyl-1H-pyrrolo[2,3-b]pyridine-2-carboxamide (31). LCMS: R$_T$=2.404 min, >98% @ 215 and 254 nm, m/z=312.0 [M+H]⁺; ¹H NMR (499 MHz, CDCl₃) δ 8.44 (dd, J=4.7, 1.6 Hz, 1H), 8.02 (dd, J=8.0, 1.6 Hz, 1H), 7.51 (d, J=8.2 Hz, 2H), 7.40 (d, J=8.3 Hz, 2H), 7.20 (dd, J=7.9, 4.7 Hz, 1H), 7.02 (s, 1H), 6.09 (s, 1H), 2.80 (dq, J=7.4, 3.7 Hz, 1H), 0.89-0.78 (m, 2H), 0.56-0.44 (m, 2H). ¹³C NMR (126 MHz, CDCl₃) b 162.26, 149.70, 146.53, 135.28, 134.13, 133.26, 130.47, 129.37, 129.08, 119.07, 117.87, 104.75, 77.29, 77.23, 77.03, 76.78, 22.81, 6.90.

1-(4-chlorophenyl)-N-cyclobutyl-1H-pyrrolo[2,3-b]pyridine-2-carboxamide (32). LCMS: R$_T$=2.582 min, >98% @ 215 and 254 nm, m/z=326.0 [M+H]⁺; ¹H NMR (499 MHz, CDCl₃) δ 8.44 (d, J=4.2 Hz, 1H), 8.04 (d, J=7.8 Hz, 1H), 7.52 (d, J=8.3 Hz, 2H), 7.41 (d, J=8.4 Hz, 2H), 7.27 (d, J=13.4 Hz, 1H), 7.20 (dd, J=7.7, 4.7 Hz, 1H), 7.06 (s, 1H), 6.06 (d, J=6.1 Hz, 1H), 4.57-4.42 (m, 1H), 2.37 (d, J=6.5 Hz, 2H), 1.88-1.78 (m, 3H), 1.78-1.70 (m, 3H). ¹³C NMR (126 MHz, CDCl₃) δ 159.88, 149.57, 146.32, 135.26, 134.17, 133.56, 130.54, 129.41, 129.09, 119.19, 117.84, 104.77, 44.88, 31.17, 15.14.

1-(4-chloro-3-fluorophenyl)-N-cyclopropyl-1H-pyrrolo[2,3-b]pyridine-2-carboxamide (33). LCMS: R$_T$=2.482 min, >98% @ 215 and 254 nm, m/z=330.0 [M+H]⁺; ¹H NMR (499 MHz, CDCl₃) δ 8.45 (s, 1H), 8.03 (d, J=7.8 Hz, 1H), 7.54 (t, J=7.6 Hz, 1H), 7.37-7.13 (m, 3H), 6.98 (s, 1H), 6.25 (s, 1H), 2.82 (s, 1H), 0.86 (d, J=7.1 Hz, 2H), 0.58 (s, 2H). ¹³C NMR (126 MHz, CDCl₃) δ 162.18, 158.82, 156.84, 149.52, 146.56, 136.50, 136.43, 133.05, 130.64, 124.34, 119.10, 118.12, 116.72, 116.54, 104.62, 22.86, 6.92.

1-(4-chloro-3-fluorophenyl)-N-cyclobutyl-1H-pyrrolo[2,3-b]pyridine-2-carboxamide (34). LCMS: R$_T$=2.643 min, >98% @ 215 and 254 nm, m/z=344.0 [M+H]⁺; ¹H NMR (499 MHz, CDCl₃) δ 8.45 (d, J=3.3 Hz, 1H), 8.06 (t, J=12.3 Hz, 1H), 7.55 (t, J=8.2 Hz, 1H), 7.31 (d, J=9.2 Hz, 1H), 7.23 (t, J=6.4 Hz, 2H), 6.19 (d, J=5.8 Hz, 1H), 4.49 (dq, J=16.0, 8.0 Hz, 1H), 2.45-2.35 (m, 2H), 1.96-1.86 (m, 2H), 1.82-1.71 (m, 2H). ¹³C NMR (126 MHz, CDCl₃) δ 159.79, 156.84, 149.41, 146.39, 133.39, 130.66, 124.29, 118.08, 116.68, 116.50, 116.41, 104.55, 77.28, 77.02, 76.77, 44.97, 31.19, 15.27.

(1-(4-chloro-3-fluorophenyl)-1H-pyrrolo[2,3-b]pyridin-2-yl)(3-fluoroazetidin-1-yl) methanone (37). LCMS: R$_T$=2.521 min, >98% @ 215 and 254 nm, m/z=348.0 [M+H]⁺; ¹H NMR (499 MHz, CDCl₃) δ 8.46 (d, J=4.0 Hz, 1H), 8.06 (dd, J=7.8, 1.6 Hz, 1H), 7.55 (t, J=8.2 Hz, 1H), 7.33 (dd, J=9.4, 2.4 Hz, 1H), 7.22 (ddd, J=11.3, 8.4, 3.8 Hz, 2H), 6.92 (s, 1H), 5.39 (ddq, J=56.6, 6.4, 3.2 Hz, 1H), 4.68-4.16 (m, 5H). ¹³C NMR (126 MHz, CDCl₃) δ 162.12, 162.10, 158.77, 156.77, 149.26, 146.86, 136.60, 136.53, 130.64, 130.56, 130.23, 124.07, 124.04, 120.91, 120.77, 119.15, 118.17, 116.45, 116.27, 106.22, 99.98, 82.82, 81.18, 29.72.

(3-fluoroazetidin-1-yl)(1-(4-methoxyphenyl)-1H-pyrrolo[2,3-b]pyridin-2-yl)methanone (38). LCMS: R$_T$=2.274 min, >98% @ 215 and 254 nm, m/z=326.0 [M+H]⁺; ¹H NMR (499 MHz, CDCl₃) δ 8.46 (dd, J=4.8, 1.6 Hz, 1H), 8.04 (dd, J=8.0, 1.7 Hz, 1H), 7.45-7.35 (m, 2H), 7.19 (d, J=7.9, 4.7 Hz, 1H), 7.10-7.02 (m, 2H), 6.90 (s, 1H), 5.32 (dtd, J=56.5, 6.2, 3.2 Hz, 1H), 4.42 (ddd, J=18.9, 12.0, 6.7 Hz, 2H), 4.35-4.16 (m, 2H), 3.89 (s, 3H). 13C NMR (126 MHz, CDCl$_3$) δ 162.95, 159.06, 149.45, 146.40, 131.08, 130.30, 129.49, 128.39, 119.10, 117.55, 114.35, 105.02, 82.81, 81.18, 55.47.

(1-(5-chloro-6-methoxypyridin-3-yl)-1H-pyrrolo[2,3-b]pyridin-2-yl)(3-fluoroazetidin-1-yl) methanone (39). LCMS: R$_T$=2.460 min, >98% @ 215 and 254 nm, m/z=361.0 [M+H]$^+$; $^1$H NMR (499 MHz, CDCl$_3$) δ 8.46 (d, J=5.0 Hz, 1H), 8.11 (d, J=2.3 Hz, 1H), 8.06 (d, J=8.0 Hz, 1H), 7.82 (d, J=2.3 Hz, 1H), 7.23 (dd, J=7.9, 4.5 Hz, 1H), 6.90 (s, 1H), 5.41 (ddt, J=56.4, 6.1, 3.0 Hz, 1H), 4.37 (d, J=133.2 Hz, 6H), 4.10 (s, 3H). $^{13}$C NMR (126 MHz, CDCl$_3$) δ 161.98, 161.96, 158.79, 149.74, 146.98, 143.25, 137.97, 130.61, 130.08, 127.68, 118.98, 118.13, 117.80, 105.98, 82.85, 81.22, 77.30, 77.05, 76.79, 54.69.

(1-(3-fluoro-4-methoxyphenyl)-1H-pyrrolo[2,3-b]pyridin-2-yl)(3-fluoroazetidin-1-yl) methanone (40). LCMS: R$_T$=2.330 min, >98% @ 215 and 254 nm, m/z=344.1 [M+H]$^+$; $^1$H NMR (499 MHz, CDCl$_3$) δ 8.46 (d, J=4.3 Hz, 1H), 8.04 (dd, J=8.0, 1.7 Hz, 1H), 7.26-7.15 (m, 3H), 7.10 (t, J=8.9 Hz, 1H), 6.89 (s, 1H), 5.36 (ddt, J=56.6, 6.2, 3.0 Hz, 1H), 4.47 (s, 3H), 4.32 (s, 3H), 3.96 (s, 3H). $^{13}$C NMR (126 MHz, CDCl$_3$) δ 162.49, 152.80, 150.83, 149.52, 147.55, 147.46, 146.67, 130.41, 129.54, 123.51, 119.01, 117.81, 116.04, 113.08, 105.43, 82.83, 81.20, 56.33.

(3-fluoroazetidin-1-yl)(1-(2-fluoropyridin-4-yl)-1H-pyrrolo[2,3-b]pyridin-2-yl)methanone (41). LCMS: R$_T$=2.157 min, >98% @ 215 and 254 nm, m/z=315.0 [M+H]$^+$; $^1$H NMR (499 MHz, CDCl$_3$) δ 8.45 (d, J=33.8 Hz, 2H), 8.07 (d, J=7.9 Hz, 1H), 7.47-7.34 (m, 1H), 7.28 (q, J=15.8, 10.9 Hz, 2H), 6.99 (s, 1H), 5.41 (dtt, J=56.3, 6.3, 3.4 Hz, 1H), 4.67-4.20 (m, 5H). $^{13}$C NMR (126 MHz, CDCl$_3$) δ 162.12, 162.10, 158.77, 156.77, 149.26, 146.86, 136.60, 136.53, 130.64, 130.56, 130.23, 124.07, 124.04, 120.91, 120.77, 119.15, 118.17, 116.45, 116.27, 106.22, 99.98, 82.82, 81.18, 29.72.

(1-(3,5-difluoro-4-methoxyphenyl)-1H-pyrrolo[2,3-b]pyridin-2-yl)(3-fluoroazetidin-1-yl) methanone (42). LCMS: R$_T$=2.456 min, >98% @ 215 and 254 nm, m/z=362.0 [M+H]$^+$; $^1$H NMR (499 MHz, CDCl$_3$) δ 8.47 (dd, J=4.7, 1.5 Hz, 1H), 8.05 (dd, J=7.9, 1.6 Hz, 1H), 7.23 (dd, J=7.9, 4.6 Hz, 1H), 7.05 (d, J=8.2 Hz, 2H), 6.89 (s, 1H), 5.41 (ddt, J=56.4, 6.1, 2.9 Hz, 1H), 4.69-4.21 (m, 5H), 4.08 (s, 3H). $^{13}$C NMR (126 MHz, CDCl$_3$) δ 162.04, 162.02, 156.27, 156.21, 154.24, 154.23, 149.32, 146.86, 136.40, 131.18, 130.62, 130.27, 119.07, 118.12, 112.43, 112.38, 112.28, 112.23, 106.05, 82.81, 81.17, 61.89, 61.86, 61.84.

(1-(3,4-dichlorobenzyl)-1H-pyrrolo[2,3-b]pyridin-2-yl)(3-fluoroazetidin-1-yl)methanone (43). To a solution of E (0.015 g; 0.068 mmol) in DMF (2.0 mL), was added 4-(bromomethyl)-1,2-dichlorobenzene (0.017 g; 0.082 mmol), 052003 (0.044 g; 0.14 mmol), and was heated in a microwave reactor at 120° C. for 1 h. Upon cooling, the solution was partitioned between EtOAc and sat NaCl. The org layer was separated, dried (MgSO$_4$), concentrated, and purified by flash chromatography on silica gel (dry loaded using silica/DCM) with a gradient of 0-70% EtOAc:Hexanes to give the corresponding target compound 43. LCMS: R$_T$=2.853 min, >98% @ 215 and 254 nm, m/z=378.0 [M+H]$^+$; $^1$H NMR (499 MHz, CDCl$_3$) δ 8.51 (dd, J=4.7, 1.6 Hz, 1H), 8.02 (dd, J=7.9, 1.6 Hz, 1H), 7.33 (dd, J=5.2, 3.1 Hz, 2H), 7.20 (dd, J=7.9, 4.7 Hz, 1H), 7.11 (dd, J=8.2, 2.1 Hz, 1H), 6.74 (s, 1H), 5.90 (s, 2H), 5.34 (ddq, J=56.6, 6.3, 3.2 Hz, 1H), 4.59-4.22 (m, 5H). $^{13}$C NMR (126 MHz, CDCl$_3$) b 163.13, 148.44, 146.29, 139.06, 132.34, 131.24, 130.51, 130.33, 129.47, 128.42, 127.08, 118.73, 117.46, 105.05, 82.82, 81.19, 45.12.

Biological Assay Data

Example 2: In Vitro PDE4 Inhibition Study

IC$_{50}$ Determination of Compound 8 on PDE4 In Vitro:

The IC$_{50}$ values of Compound 8 on PDE4 isoforms were determined by BPS Bioscience, San Diego. In brief, coat proteins (PDE4 isoforms) were added into the plate in a volume of 50 μl (2-5 ng/μl) at 4° C. overnight. The next day, Compound 8 was added to the coated plate with varying concentrations followed by addition of the corresponding biotinylated binding partner. The reaction was incubated for 2 hours at room temperature. Binding assays were performed in duplicate at each concentration and the plates were read by using Synergy 2 BioTek plate reader. The luminescence data were analyzed using the Graphpad Prism. Percent inhibition was determined by normalizing the data to signal from negative control wells (uncoated wells treated with the biotinylated ligand, set as 100% inhibition) and positive control wells (coated wells treated with the biotinylated ligand in the absence of any inhibitor, set as 0% inhibition). Data for a reference compounds or antibodies are included as a control for inhibition. Results are presented in Table B, below. "ND" indicates the compound was not tested.

TABLE B

| | IC$_{50}$, nM; (% Inhibition @ 10 μM) | |
|---|---|---|
| Compound # | PDE4B | PDE4D |
| 1 | 630 | (59) |
| 2 | 1,100 | (24) |
| 3 | 600 | (36) |
| 4 | (23) | (11.6) |
| 5 | (70) | (52) |
| 6 | 110 | 450 |
| 7 | 230 | (77) |
| 8 | 140 | 880 |
| 9 | 430 | 1,000 |
| 10 | (73) | (39) |
| 11 | (39) | (17) |
| 12 | (50) | (29) |
| 13 | 980 | ~2,300 |
| 14 | (20) | (6) |
| 15 | (33) | (13) |
| 16 | 480 | (41) |
| 17 | 2,300 | (43) |
| 18 | 9,400 | (25.6) |
| 19 | ND | ND |
| 20 | 910 | (60) |
| 21 | 1,400 | (53) |
| 22 | 1,300 | (10.7) |
| 23 | ND | ND |
| 24 | ND | ND |
| 25 | 210 | (62) |
| 26 | 1,400 | (18.5) |
| 27 | 1,800 | (16.6) |
| 28 | (58) | (12.1) |
| 29 | (47) | (18) |
| 30 | 430 | (66) |
| 31 | 2,900 | (10.1) |
| 32 | 5,000 | (28.2) |
| 33 | 970 | (24) |
| 34 | 1,300 | (39) |
| 35 | ND | ND |
| 36 | ND | ND |
| 37 | 610 | (71) |
| 38 | (67) | (37) |
| 39 | 490 | 1,600 |
| 40 | (77) | (52) |
| 41 | 980 | ~1,900 |
| 42 | 410 | ~6,300 |
| 43 | (72) | (58) |

Example 3: Cell-Based Growth Inhibition Assays $EC_{50}$ Detection of Compound 8 In Vitro:

HEK293 cells were cultured in growth media (10% fetal bovine serum, 1% Pen-Strep, 1% Non-essential amino acids, 1 mM Na-pyruvate) and seeded at 30,000 cells/well into 96-well microplate. Cells were incubated at 37° C. and 5% $CO_2$ overnight. The following day, the cells were transfected with PDE4B1 expression vector, CRE luciferase reporter and a control Renilla luciferase vector using Lipofectamine 2000 and Opti-MEM for 6 h. The media was removed and the cells were dosed with test compounds or controls in 50 µl of fresh growth medium and incubated overnight. The next day, forskolin was added in 5 µl of growth medium to stimulated wells at a final concentration of 10 µM for 5-6 h. After treatment, a dual luciferase assay was performed using BPS Bioscience Dual Luciferase assay system: 55 µl of firefly luciferase reagent per well was added to measure firefly luminescence. Subsequently, another 55 µl/well of Renilla luciferase reagent was added to measure Renilla luminescence. Cell based assays were performed in triplicate at each concentration. To obtain the normalized luciferase activity of CRE reporter, subtract background luminescence then calculate the ratio of firefly luminescence from the CRE reporter to Renilla luminescence from the control Renilla luciferase vector. The normalized luciferase activity data was analyzed, and the $EC_{50}$ value was determined by the concentration causing a half-maximal percent activity.

Compound 8 was shown to have a ten-fold lower $EC_{50}$ for PDE4B inhibition than apremilast, a PDE4 inhibitor approved for treating psoriasis and psoriatic arthritis, Results are presented in Table C, below.

TABLE C

| Cell-based PDE4B assay ($EC_{50}$, mM) | |
|---|---|
| Compound 8 | 0.5 |
| Apremilast | 5.0 |

Example 4: Macrophage Inhibition Study

Bone marrow-derived macrophages were unstimulated (-) or pre-treated with the indicated concentrations of the well-characterized PDE4 inhibitor rolipram or target compounds (1 or 10 µM) for 30 min prior to LPS (100 ng/ml; A) or Pam3Cys (10 µg/ml; B) stimulation. After a 24 h treatment period, conditioned medium was collected to quantitate TNF-α expression by ELISA. Results are reported as the mean values (±SD) from 3 independent replicates for each treatment and were repeated in two separate experiments. *, $p<0.05$; , $p<0.01$; *, $p<0.001$; ****, $p<0.0001$; One-way ANOVA with Dunnett's multiple comparisons post-hoc analysis.

Preparation of Mouse Bone Marrow-Derived Macrophages and Evaluation of PDE4 Inhibitors on Macrophage Pro-Inflammatory Activity Macrophages were expanded from the bone marrow of C57BL/6 mice as previously described. Briefly, bone marrow was flushed from femurs with sterile RPMI-1640 serum-free medium and cultured in RPMI-1640 containing 10% FBS, penicillin/streptomycin/fungizone, and 5% conditioned medium from L929 fibroblasts as a source of macrophage-colony stimulating factor (M-CSF). After a 6 day expansion period, macrophages were harvested and plated in a 96-well plate at $5 \times 10^4$ cells/well. The following day, macrophages were pre-treated with various concentrations of rolipram or the novel PDE4 inhibitors described in this report (1 or 10 µM) for 30 min prior to stimulation with LPS (100 ng/ml) or Pam3Cys (10 µg/ml). After a 24 h treatment period, conditioned medium was assessed for TNF-☐ release by enzyme-linked immunosorbent assay (ELISA). Controls included unstimulated macrophages or cells exposed to PDE4 inhibitors alone.

Since PDE4 inhibitors have well-documented anti-inflammatory properties, their ability of these compounds to inhibit macrophage pro-inflammatory activity was studied by measuring the production of the classical pro-inflammatory cytokine TNF-α (FIG. 1). Two well-characterized pro-inflammatory stimuli were tested, namely lipopolysaccharide (LPS) and a synthetic lipopeptide (Pam3Cys) that represent prototypical bacterial ligands for Toll-like receptors 4 and 2, respectively (TLR4 and TLR2). All of the test compounds inhibited TNF-α production by mouse bone marrow-derived macrophages to the same extent, or better than, the well-characterized PDE4 inhibitor, rolipram (FIG. 1). A dose-dependent response was observed with regard to LPS-induced TNF-α release, where higher concentrations were less effective across the group of compounds (FIG. 1A), which has been reported with other PDE4 inhibitors. A similar dose-response was observed with some compounds when macrophages were stimulated with Pam3Cys (FIG. 1B); nevertheless, cytokine production was significantly reduced across the compound class. None of the compounds elicited TNF-α production when tested alone (data not shown). Collectively, these findings support the biological action of the target compounds, which model the anti-inflammatory actions of the well-characterized PDE4 inhibitor rolipram.

Example 5: Mouse Cocaine Studies

Locomotor analysis: WT mice (both gender, n=6-8) were divided into four groups receiving various treatments: (1) vehicle+saline; (2) vehicle+cocaine; (3) Compound 8+saline; and (4) Compound 8+cocaine. Cocaine was administered at 20 mg/kg (i.p.) and Compound 8 was used at two different doses 5 or 10 mg/kg (i.p.). Compound 8 was firstly injected into the mice and 30 min later followed with cocaine administration. To investigate the effects of Compound 8 on acute locomotor response, immediately following cocaine injection, mice were put into the open field apparatus (Truescan, Coulbourn instrument) to detect locomotor activity for 45 min. The TruScan photobeam activity system consists of a clear arena with infrared sensors located on a ring 3 cm above floor level. There are 16 beams spaced 1 inch apart on the sensor ring that are used to detect movements by mice. These data are automatically relayed to a PC computer and interpreted by software. To investigate the effects of Compound 8 on locomotor sensitization, mice were repeatedly injected with Compound 8 and cocaine for 7 consecutive days and the locomotor responses were recorded every other day.

Self-Administration:

(a) Surgery procedure: WT mice (10-12 weeks, both genders) were implanted with permanently indwelling catheters (Plastics one) into the right jugular vein under a combination of ketamine hydrochloride (100 mg/mg, i. p.) and xylazine (10 mg/mg, i.p.) anesthesia. The catheter is tied to the vein with surgical silk and is passed subcutaneously to the back of the mouse where the catheter is affixed to a small plastic pedestal (26 G, Plastics One Company). After the surgery, the catheters were flushed daily with heparin (30

IU/mi) to avoid clotting. Mice were allowed at least 7 days of recovery in their home before the start of the experiments.

(b) The establishment of cocaine self-administered mice: Mice were individually put into sound-mitigation cubicles (Coulbourne Instrument) for the training of self-administered cocaine (1.0 mg/kg/infusion). Mice were reinforced for nose-poking the cue-paired (active) sensor by delivery of intravenous cocaine in 5 second with 20 µl solution while nose-poking the inactive sensor resulted in no consequence. A timeout period of 15 seconds followed each drug injection. All responses were recorded automatically using a computer interface and Graphic State Notation 4 software (Coulbourne Instrument). Mice were trained to self-administer cocaine during one daily session under a fixed ratio 1 (FR1) schedule. Each session lasted for a maximum of 2 h or until the mice received 30 cocaine infusions to avoid overdose. The acquisition period was conducted for 7-10 days to help mice perform stable cocaine self-intake under the following criteria: (1) the ratio of active poke vs. inactive poke is above 2:1; (2) the minimum of cocaine infusions is above 10; and (3) the variation for cocaine intake for consecutive three days is below 20%. After the establishment of cocaine intake, mice were under an FR1 schedule for an additional one week of cocaine self-administration (daily 2 h sessions, 1.0 mg/kg/infusion). Mice were flushed before and after each session and after the last session, mice were administered with ketamine to affirm the patency of catheter setup.

(c) The effects of Compound 8 on cocaine-mediated seeking and taking behavior. Compound 8/vehicle was injected into cocaine self-administered mice (i.p.) and 30 min later, mice were put into cubicle for 2 h under FR1 schedule. The numbers of active nose-poke and cocaine infusions were recorded. Mice with vehicle injection served as controls.

Figure 2:
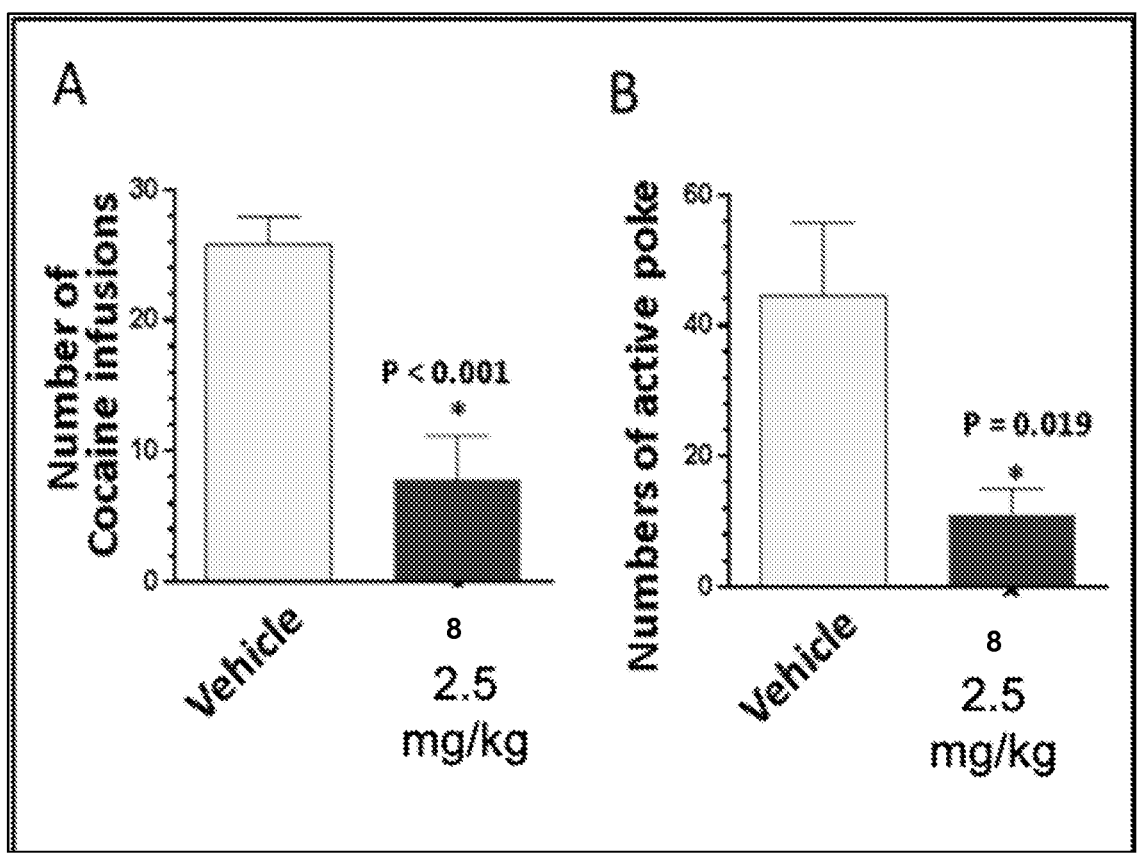
FIG. 2 shows that compound 8 significantly decreased the cocaine-mediated seeking and taking behavior in mice.
Figure 3:
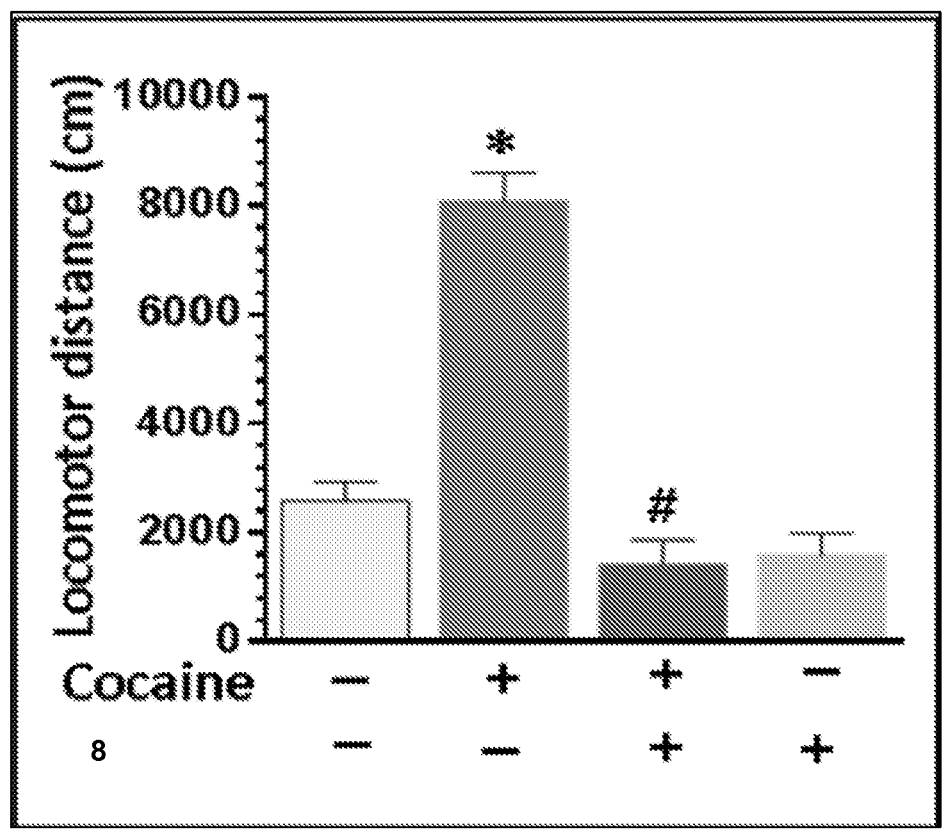
FIG. 3 shows that compound 8 inhibited the cocaine induce hyperlocomotion without any increase by itself.

Compound 8 significantly decreased the cocaine-mediated seeking and taking behavior in mice (FIG. 2), and inhibited the cocaine induce hyperlocomotion without any increase alone (FIG. 3).

In view of the many possible embodiments to which the principles of the disclosure may be applied, it should be recognized that the illustrated embodiments are only examples and should not be taken as limiting the scope of the invention.

What is claimed:

1. A compound, or a pharmaceutically acceptable salt thereof, having a structure of Formula (I):

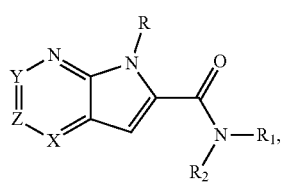

wherein
X, Y, and Z are each $CR_3$;
R is $C_{0-6}$alkylene-$C_{6-10}$aryl optionally substituted by 1-3 $R_4$;
$R_1$ and $R_2$ together with the nitrogen atom to which they are attached form a 3-10 membered heterocycloalkyl ring comprising 0-2 additional ring heteroatoms independently selected from N, O, and S, wherein the heterocycloalkyl is optionally substituted by 1-3 $R_6$;

each $R_3$ is independently H, $C_{1-6}$alkyl, halogen, $CF_3$, OH, CN, $CONR_7(R_7)$, $SO_2NR_7R_7$, O—$C_{1-6}$alkyl, or O—$C_{6-10}$aryl, and the aryl is optionally substituted with 1-3 $R_5$;

each $R_4$ is independently $C_{1-6}$alkyl, halogen, $CF_3$, CN, $CONHR_7$, $SO_2NR_7R_7$, O—$C_{1-6}$alkyl, or O—$C_{6-10}$aryl;

each of $R_5$ and $R_6$ is independently $C_{1-6}$alkyl, halogen, $CF_3$, CN, OH, or O—$C_{1-6}$alkyl; and each $R_7$ is independently H, $C_{1-6}$alkyl, $C_{0-6}$alkylene-$C_{6-10}$aryl, $C_{0-6}$alkylene-5-7 membered heteroaryl, $C_{0-6}$alkylene-$C_{3-10}$cycloalkyl, or $C_{0-6}$alkylene-3-10 membered heterocycloalkyl, each aryl, heteroaryl, cycloalkyl, and heterocycloalkyl is optionally substituted by 1-3 $R_5$, and the heteroaryl and heterocycloalkyl comprise 1-4 ring heteroatoms independently selected from N, O, and S.

2. The compound or salt of claim 1, wherein each $R_3$ is independently H, $C_{1-6}$alkyl, halogen, $CF_3$, OH, CN, or O—$C_{1-6}$alkyl.

3. The compound or salt of claim 2, wherein X, Y, and Z are each CH.

4. The compound or salt of claim 1, wherein R is $C_{6-10}$aryl.

5. The compound or salt of any claim 1, wherein R is phenyl.

6. The compound or salt of claim 1, wherein R is substituted by 1 to 3 $R_4$.

7. The compound or salt of claim 1, wherein each $R_4$ is independently $C_{1-6}$alkyl, O—$C_{1-6}$alkyl, halogen, or CN.

8. The compound or salt of claim 7, wherein at least one $R_4$ is fluoro, chloro, methyl, CN, or OMe.

9. The compound or salt of claim 1, wherein R is

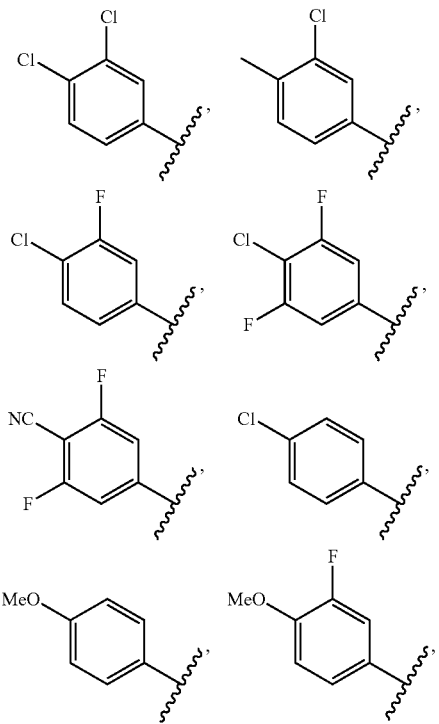

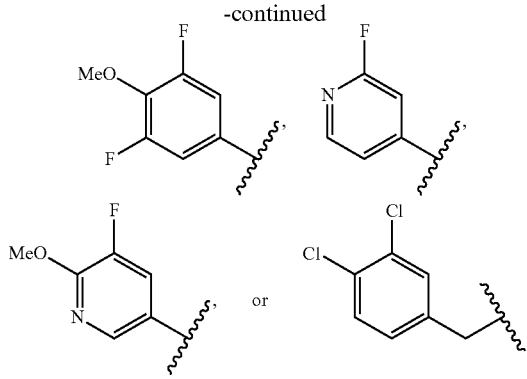

10. The compound or salt of claim 9, wherein R is

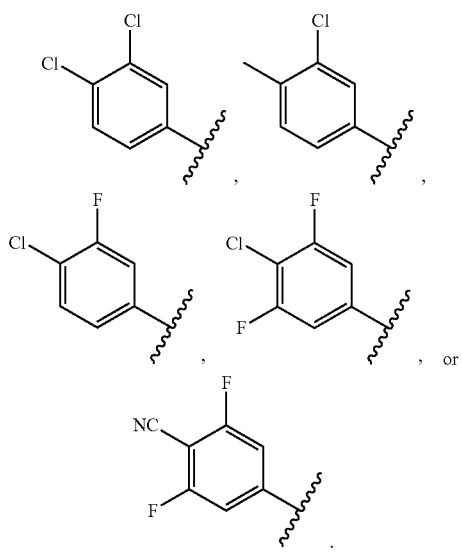

11. The compound or salt of claim 1, wherein R is dichlorophenyl.

12. The compound or salt of claim 1, wherein the heterocycloalkyl ring formed by $R_1$ and $R_2$ together with the nitrogen atom to which they are attached is unsubstituted.

13. The compound or salt of claim 1, wherein the heterocycloalkyl ring formed by $R_1$ and $R_2$ together with the nitrogen atom to which they are attached is substituted by 1-3 $R_6$.

14. The compound or salt of claim 13, wherein $R_6$ is halogen or $CF_3$.

15. The compound or salt of claim 13, wherein $R_6$ is fluoro.

16. The compound or salt of claim 14, wherein at least one $R_6$ is $CF_3$.

17. The compound or salt of claim 1, wherein $N(R_1)(R_2)$ is

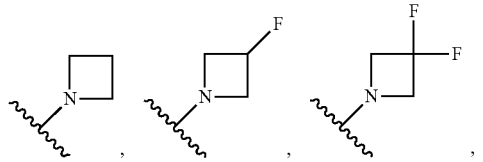

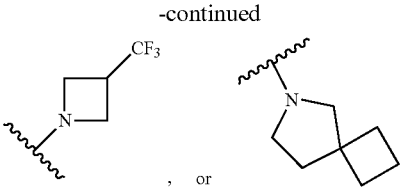

18. A compound selected from compounds 6-12, 14, 15, 25, 30, 37, and 38:

| Compound # | Structure |
|---|---|
| 6 | 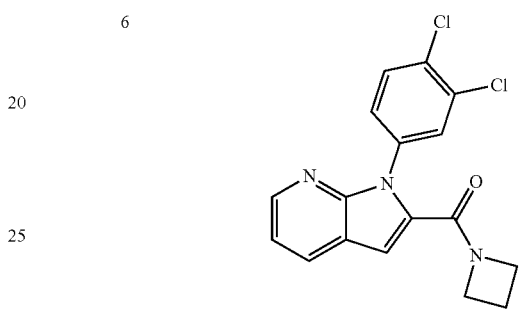 |
| 7 | 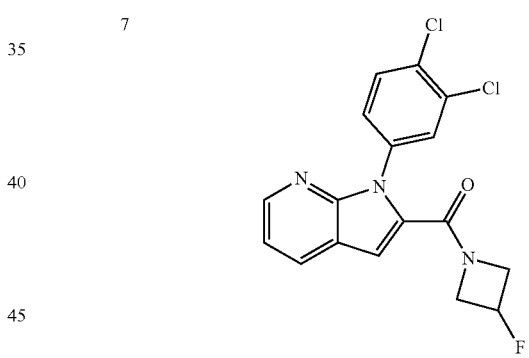 |
| 8 | 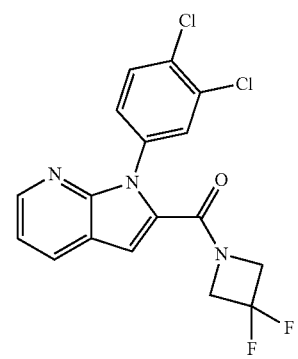 [SMILES: O=C(c1cc2cccnc2n1-c1ccc(Cl)c(Cl)c1)N1CC(F)(F)C1] |

| Compound # | Structure |
|---|---|
| 9 | 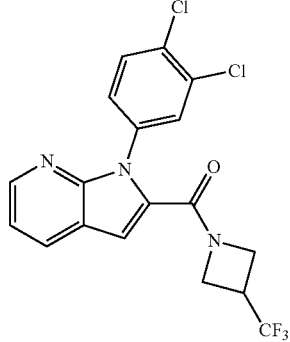 [SMILES: O=C(c1cc2cccnc2n1-c1ccc(Cl)c(Cl)c1)N1CC(C(F)(F)F)C1] |
| 10 | 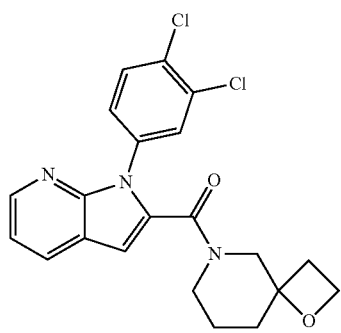 [SMILES: O=C(c1cc2cccnc2n1-c1ccc(Cl)c(Cl)c1)N1CCCC2(CCO2)C1] |
| 11 | 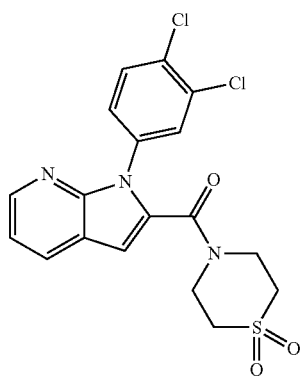 [SMILES: O=C(c1cc2cccnc2n1-c1ccc(Cl)c(Cl)c1)N1CCS(=O)(=O)CC1] |
| 12 | 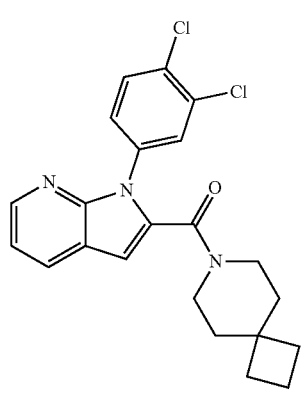 [SMILES: O=C(c1cc2cccnc2n1-c1ccc(Cl)c(Cl)c1)N1CCC2(CCC2)CC1] |
| Compound # | Structure |
|---|---|
| 14 | 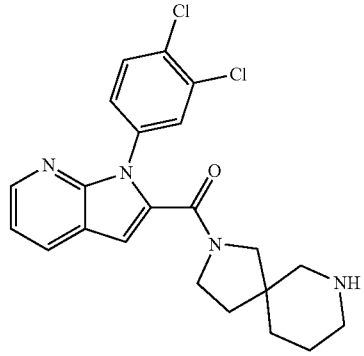 [SMILES: O=C(c1cc2cccnc2n1-c1ccc(Cl)c(Cl)c1)N1CCC2(CCCNC2)C1] |
| 15 | 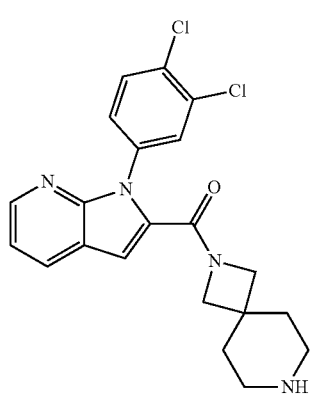 [SMILES: O=C(c1cc2cccnc2n1-c1ccc(Cl)c(Cl)c1)N1CC2(CCNCC2)C1] |
| 25 | 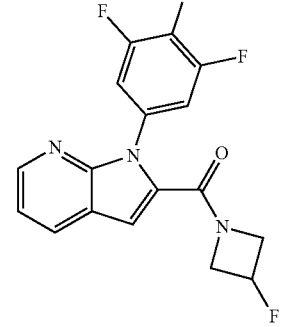 |
| 30 | 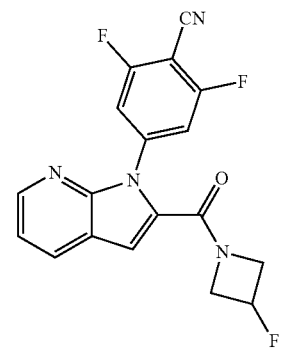 [SMILES: N#Cc1c(F)cc(-n2c(C(=O)N3CC(F)C3)cc3cccnc32)cc1F] |

-continued
| Compound # | Structure |
|---|---|
| 37 | 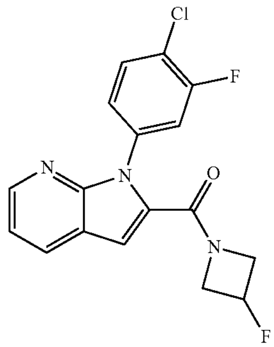 [SMILES: O=C(c1cc2cccnc2n1-c1ccc(Cl)c(F)c1)N1CC(F)C1] |
| 38 | 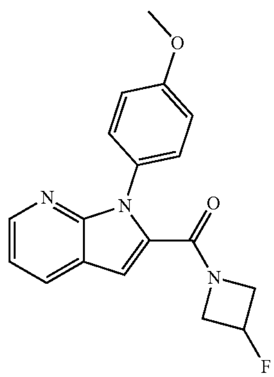 [SMILES: COc1ccc(-n2c(C(=O)N3CC(F)C3)cc3cccnc32)cc1] |
| 42 |  |
| 43 | |
19. A pharmaceutical formulation comprising the compound or salt of claim 1 and a pharmaceutically acceptable excipient.
* * * * *